US012576064B2

(12) United States Patent
Rinsch et al.

(10) Patent No.: US 12,576,064 B2
(45) Date of Patent: Mar. 17, 2026

(54) UROLITHIN GUMMY (PECTIN) FORMULATIONS

(71) Applicant: Amazentis SA, Lausanne (CH)

(72) Inventors: Christopher L. Rinsch, Lausanne (CH); Anurag Singh, Lausanne (CH); William Blanco-Bose, La Croix (CH); Davide D'Amico, Renens (CH); Alan McClure, Columbia, MO (US)

(73) Assignee: Amazentis SA, Lausanne (CH)

( * ) Notice: Subject to any disclaimer, the term of this patent is extended or adjusted under 35 U.S.C. 154(b) by 0 days.

(21) Appl. No.: 19/311,629

(22) Filed: Aug. 27, 2025

(65) Prior Publication Data

US 2025/0375412 A1 Dec. 11, 2025

Related U.S. Application Data

(63) Continuation of application No. 18/680,751, filed on May 31, 2024.

(30) Foreign Application Priority Data

Jun. 1, 2023 (GB) ..................................... 2308224

(51) Int. Cl.

| | |
|---|---|
| ***A61K 31/352*** | (2006.01) |
| ***A61K 9/00*** | (2006.01) |
| ***A61K 47/12*** | (2006.01) |
| ***A61K 47/26*** | (2006.01) |
| ***A61K 47/46*** | (2006.01) |

(52) U.S. Cl.
CPC .......... *A61K 31/352* (2013.01); *A61K 9/0056* (2013.01); *A61K 47/12* (2013.01); *A61K 47/26* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 5,073,545 | A | 12/1991 | Arima et al. |
| 5,411,757 | A | 5/1995 | Buist et al. |
| 6,066,312 | A | 5/2000 | Egawa et al. |
| 6,133,311 | A | 10/2000 | Bok et al. |
| 6,440,436 | B1 | 8/2002 | Ghosal |
| 8,183,282 | B2 | 5/2012 | Seeram et al. |
| 8,894,993 | B2 | 11/2014 | Ghosal |
| 8,933,217 | B2 | 1/2015 | Rinsch et al. |
| 9,394,269 | B2 | 7/2016 | Rinsch et al. |
| 9,573,922 | B2 | 2/2017 | Rinsch et al. |
| 9,872,850 | B2 | 1/2018 | Rinsch et al. |
| 9,962,366 | B2 | 5/2018 | Rinsch et al. |
| 9,980,980 | B2 | 5/2018 | Rinsch et al. |
| 9,994,542 | B2 | 6/2018 | Rinsch et al. |
| 10,028,932 | B2 | 7/2018 | Rinsch et al. |
| 10,442,784 | B2 | 10/2019 | Andreux et al. |
| 10,485,782 | B2 | 11/2019 | Rinsch et al. |
| 10,532,992 | B2 | 1/2020 | Rinsch et al. |
| 10,695,320 | B2 | 6/2020 | Andreux et al. |
| 10,792,276 | B2 | 10/2020 | Singh et al. |
| 10,857,126 | B2 | 12/2020 | Rinsch et al. |
| 10,906,883 | B2 | 2/2021 | Skranc et al. |
| 10,988,453 | B2 | 4/2021 | Andreux et al. |
| 11,020,373 | B2 | 6/2021 | Rinsch et al. |
| 11,166,937 | B2 | 11/2021 | Rinsch et al. |
| 11,166,972 | B2 | 11/2021 | Andreux et al. |
| 11,180,468 | B2 | 11/2021 | Rinsch et al. |
| 11,234,960 | B2 | 2/2022 | Rinsch et al. |
| 11,337,957 | B2 | 5/2022 | Andreux et al. |
| 11,426,380 | B2 | 8/2022 | Singh et al. |
| 11,634,401 | B2 | 4/2023 | Skranc et al. |
| 11,878,964 | B2 | 1/2024 | Andreux et al. |
| 11,903,922 | B2 | 2/2024 | Rinsch et al. |
| 11,925,616 | B2 | 3/2024 | Andreux et al. |
| 11,931,335 | B2 | 3/2024 | Rinsch et al. |
| 11,931,336 | B2 | 3/2024 | Rinsch et al. |
| 11,969,408 | B2 | 4/2024 | Rinsch et al. |
| 12,030,863 | B2 | 7/2024 | Rinsch et al. |
| 12,036,205 | B2 | 7/2024 | Rinsch et al. |
| 12,109,190 | B2 | 10/2024 | Singh et al. |

(Continued)

FOREIGN PATENT DOCUMENTS

| | | | |
|---|---|---|---|
| CN | 101301319 | A | 11/2008 |
| CN | 101484125 | A | 7/2009 |

(Continued)

OTHER PUBLICATIONS

Mitopure Gummies, accessed online Oct. 6, 2025 (Year: 2025).*
Singh et al. (Direct Supplementation with Urolithin A overcomes limitations of dietary exposure and gut microbiome variability in healthy adults to achieve consistent levels across the population, European Journal of Clinical Nutrition 76, 297-308 (2022); published Jun. 11, 2021). (Year: 2021).*
"Questions and Answers on Dietary Supplements." FDA, 2024. https://www.fda.gov/food/information-consumers-using-dietary-supplements/questions-and-answers-dietary-supplements.
Abstract of unexamined Japanese application No. JP2010-280627 published Dec. 16, 2010.

(Continued)

*Primary Examiner* — Melissa S Mercier
(74) *Attorney, Agent, or Firm* — Foley Hoag LLP; Dana M. Gordon; Lawrence P. Tardibono

(57) ABSTRACT

The invention relates to composition of urolithins comprising urolithins and pectin and formulations of urolithins, specifically chewable formulations, comprising urolithins and a gelling agent. The invention further comprises compositions and chewable formulations comprising urolithins in combination with other active ingredients and processes for the preparation of such compositions and formulations. The invention further comprises methods of using such compositions and formulations in the treatment of conditions and diseases and for the promotion of health and performance, such in the improving muscle function.

30 Claims, 10 Drawing Sheets

(56) References Cited

U.S. PATENT DOCUMENTS

| | | | |
|---|---|---|---|
| 12,220,424 B2 | 2/2025 | Andreux et al. | |
| 12,297,182 B2 | 5/2025 | Andreux et al. | |
| 12,310,943 B2 | 5/2025 | Rinsch et al. | |
| 12,338,224 B2 | 6/2025 | Skranc et al. | |
| 2003/0039662 A1 | 2/2003 | Ghosal | |
| 2003/0078212 A1 | 4/2003 | Li et al. | |
| 2005/0234031 A1 | 10/2005 | Schrimpf et al. | |
| 2005/0282781 A1 | 12/2005 | Ghosal | |
| 2006/0257337 A1 | 11/2006 | Sherris | |
| 2007/0148292 A1* | 6/2007 | Royo | A23G 3/44 426/103 |
| 2007/0184136 A1 | 8/2007 | Aviram | |
| 2007/0197567 A1 | 8/2007 | Sherris | |
| 2008/0031862 A1 | 2/2008 | Ghosal | |
| 2008/0039179 A1 | 2/2008 | Seelig et al. | |
| 2008/0206275 A1 | 8/2008 | Ramazanov et al. | |
| 2008/0213401 A1 | 9/2008 | Smith | |
| 2008/0214656 A1 | 9/2008 | Lim et al. | |
| 2009/0246300 A1 | 10/2009 | Swilling | |
| 2009/0326057 A1 | 12/2009 | Seeram et al. | |
| 2010/0004334 A1 | 1/2010 | Jouni et al. | |
| 2010/0021533 A1 | 1/2010 | Mazed et al. | |
| 2010/0055247 A1 | 3/2010 | Tirrito | |
| 2011/0065662 A1 | 3/2011 | Rinsch et al. | |
| 2011/0263521 A1 | 10/2011 | Moutet et al. | |
| 2012/0164243 A1 | 6/2012 | Rinsch et al. | |
| 2014/0018415 A1 | 1/2014 | Rinsch et al. | |
| 2014/0100270 A1 | 4/2014 | Sherris | |
| 2015/0104539 A1* | 4/2015 | Daniels | A23L 33/15 426/302 |
| 2015/0183758 A1 | 7/2015 | Rinsch et al. | |
| 2015/0196577 A1 | 7/2015 | Rinsch et al. | |
| 2016/0000753 A1 | 1/2016 | Rinsch et al. | |
| 2016/0095881 A1 | 4/2016 | Sen | |
| 2016/0183758 A1 | 6/2016 | Baker et al. | |
| 2016/0213641 A1 | 7/2016 | Rinsch et al. | |
| 2016/0213643 A1 | 7/2016 | Rinsch et al. | |
| 2016/0326131 A1 | 11/2016 | Rinsch et al. | |
| 2016/0332982 A1 | 11/2016 | Rinsch et al. | |
| 2017/0143666 A1 | 5/2017 | Rinsch et al. | |
| 2017/0143667 A1 | 5/2017 | Rinsch et al. | |
| 2018/0000753 A1 | 1/2018 | Tønnesen et al. | |
| 2018/0015069 A1 | 1/2018 | Rinsch et al. | |
| 2018/0213641 A1 | 7/2018 | Hosoda et al. | |
| 2018/0243261 A1 | 8/2018 | Andreux et al. | |
| 2018/0256471 A1 | 9/2018 | Rinsch et al. | |
| 2018/0256538 A1 | 9/2018 | Rinsch et al. | |
| 2018/0256539 A1 | 9/2018 | Rinsch et al. | |
| 2018/0296464 A1 | 10/2018 | Graban et al. | |
| 2018/0303794 A1 | 10/2018 | Rinsch et al. | |
| 2018/0332982 A1 | 11/2018 | Son et al. | |
| 2019/0000867 A1 | 1/2019 | Rinsch et al. | |
| 2019/0008883 A1 | 1/2019 | Andreux et al. | |
| 2019/0010138 A1 | 1/2019 | Rinsch et al. | |
| 2019/0040031 A1 | 2/2019 | Nakajima | |
| 2019/0062297 A1* | 2/2019 | Andreux | A61K 38/01 |
| 2019/0143667 A1 | 5/2019 | Boje et al. | |
| 2019/0263772 A1 | 8/2019 | Skranc et al. | |
| 2019/0328703 A1 | 10/2019 | Singh et al. | |
| 2020/0010138 A1 | 1/2020 | Nishihara et al. | |
| 2020/0085895 A1 | 3/2020 | Patel et al. | |
| 2020/0140405 A1 | 5/2020 | Andreux et al. | |
| 2020/0223813 A1 | 7/2020 | Rinsch et al. | |
| 2020/0243261 A1 | 7/2020 | Berolini et al. | |
| 2020/0323818 A1 | 10/2020 | Andreux et al. | |
| 2020/0328703 A1 | 10/2020 | Hille | |
| 2020/0397748 A1 | 12/2020 | Rinsch et al. | |
| 2021/0008883 A1 | 1/2021 | Sakaida et al. | |
| 2021/0018415 A1 | 1/2021 | Jiang et al. | |
| 2021/0059982 A1 | 3/2021 | Rinsch et al. | |
| 2021/0085642 A1 | 3/2021 | Singh et al. | |
| 2021/0140405 A1 | 5/2021 | Hansen et al. | |
| 2021/0198225 A1 | 7/2021 | Skranc et al. | |
| 2021/0210190 A1 | 7/2021 | Rinsch et al. | |
| 2021/0223813 A1 | 7/2021 | Neumann et al. | |
| 2021/0251869 A1 | 8/2021 | Rinsch et al. | |
| 2021/0263772 A1 | 8/2021 | Televitckiy et al. | |
| 2021/0303794 A1 | 9/2021 | Contreras et al. | |
| 2021/0346342 A1 | 11/2021 | Rinsch et al. | |
| 2021/0353591 A1 | 11/2021 | Rinsch et al. | |
| 2021/0369805 A1 | 12/2021 | Wan et al. | |
| 2022/0073488 A1 | 3/2022 | Andreux et al. | |
| 2022/0105117 A1 | 4/2022 | Andreux et al. | |
| 2022/0127240 A1 | 4/2022 | Rinsch et al. | |
| 2022/0280410 A1 | 9/2022 | Perretta et al. | |
| 2022/0280475 A1 | 9/2022 | Rinsch et al. | |
| 2022/0323407 A1 | 10/2022 | Andreux et al. | |
| 2023/0097072 A1 | 3/2023 | Singh et al. | |
| 2023/0233523 A1 | 7/2023 | Rinsch et al. | |
| 2023/0277669 A1 | 9/2023 | Rinsch et al. | |
| 2023/0301890 A1 | 9/2023 | Rinsch et al. | |
| 2023/0355501 A1 | 11/2023 | Ookura et al. | |
| 2023/0357176 A1 | 11/2023 | Skranc et al. | |
| 2023/0390238 A1 | 12/2023 | Rinsch et al. | |
| 2024/0100016 A1 | 3/2024 | Rinsch et al. | |
| 2024/0130980 A1 | 4/2024 | Warrington et al. | |
| 2024/0148690 A1 | 5/2024 | Andreux et al. | |
| 2024/0150310 A1 | 5/2024 | Andreux et al. | |
| 2024/0156777 A1 | 5/2024 | Rinsch et al. | |
| 2024/0366558 A1 | 11/2024 | Rinsch et al. | |
| 2025/0049750 A1 | 2/2025 | Rinsch et al. | |
| 2025/0161391 A1 | 5/2025 | Rinsch et al. | |
| 2025/0213524 A1 | 7/2025 | Rinsch et al. | |
| 2025/0228816 A1 | 7/2025 | Rinsch et al. | |
| 2025/0228817 A1 | 7/2025 | Rinsch et al. | |

FOREIGN PATENT DOCUMENTS

| | | | |
|---|---|---|---|
| CN | 101541182 | A | 9/2009 |
| CN | 103442594 | A | 12/2013 |
| CN | 109316478 | A | 2/2019 |
| CN | 110368476 | A | 10/2019 |
| CN | 112843049 | A | 5/2021 |
| CN | 113171319 | A | 7/2021 |
| CN | 113476362 | A | 10/2021 |
| CN | 113855758 | A | 12/2021 |
| CN | 114794490 | A | 7/2022 |
| CN | 115868614 | A | 3/2023 |
| CN | 115887392 | A | 4/2023 |
| CN | 116889583 | A | 10/2023 |
| EP | 2033526 | A1 | 3/2009 |
| EP | 2068864 | A2 | 6/2009 |
| EP | 2654461 | A2 | 10/2013 |
| EP | 3278800 | A2 | 2/2018 |
| JP | H02304080 | A | 12/1990 |
| JP | 2008-503456 | A | 2/2008 |
| JP | 2010-280627 | A | 12/2010 |
| JP | 2016-216378 | A | 12/2016 |
| JP | 2017-007951 | A | 1/2017 |
| JP | 2017-014154 | A | 1/2017 |
| JP | 2017-019725 | A | 1/2017 |
| JP | 6054301 | B2 | 1/2017 |
| JP | 2017-031108 | A | 2/2017 |
| JP | 2022-185501 | A | 12/2022 |
| WO | WO-00/06134 | A2 | 2/2000 |
| WO | WO-00/15044 | A1 | 3/2000 |
| WO | WO-01/49281 | A2 | 7/2001 |
| WO | WO-02/094984 | A2 | 11/2002 |
| WO | WO-2003/013438 | A2 | 2/2003 |
| WO | WO-2005/077899 | A2 | 8/2005 |
| WO | WO-2005/097106 | A1 | 10/2005 |
| WO | WO-2006/007310 | A2 | 1/2006 |
| WO | WO-2006/127832 | A2 | 11/2006 |
| WO | WO-2007/101247 | A2 | 9/2007 |
| WO | WO-2007/127263 | A2 | 11/2007 |
| WO | WO-2008/016554 | A1 | 2/2008 |
| WO | WO-2007/133249 | A3 | 2/2009 |
| WO | WO-2009/031023 | A2 | 3/2009 |
| WO | WO-2009/120799 | A2 | 10/2009 |
| WO | WO-2009/153652 | A2 | 12/2009 |
| WO | WO-2011/011721 | A2 | 1/2011 |
| WO | WO-2012/088519 | A2 | 6/2012 |
| WO | WO-2012/103487 | A1 | 8/2012 |
| WO | WO-2012/113835 | A1 | 8/2012 |

(56) References Cited

FOREIGN PATENT DOCUMENTS

| | | | |
|---|---|---|---|
| WO | WO-2012/156600 | A1 | 11/2012 |
| WO | WO-2014/004902 | A2 | 1/2014 |
| WO | WO-2015/100213 | A2 | 7/2015 |
| WO | WO-2017/109195 | A1 | 6/2017 |
| WO | WO-2018/162650 | A1 | 9/2018 |
| WO | WO-2018/162651 | A1 | 9/2018 |
| WO | WO-2019/168972 | A1 | 9/2019 |
| WO | WO-2021/237214 | A1 | 11/2021 |
| WO | WO-2022 / 063846 | A1 | 3/2022 |
| WO | WO-2023/031673 | A1 | 3/2023 |
| WO | WO-2023/237926 | A2 | 12/2023 |
| WO | WO-2024/246601 | A1 | 12/2024 |
| WO | WO-2024/246603 | A1 | 12/2024 |
| WO | WO-2025/078619 | A1 | 4/2025 |
| WO | WO-2025/078645 | A1 | 4/2025 |

OTHER PUBLICATIONS

Adams et al., "Pomegranate Ellagitannin-Derived Compounds Exhibit Antiproliferative and Antiaromatase Activity in Breast Cancer Cells In Vitro," Cancer Prev Res, 3: 108-113 (2010).

Andreux et al., "Appendix A: The mitophagy activator urolithin A is safe and induces a molecular signature of improved mitochondrial and cellular health in humans," Nature Metabolish, 1:595-603 (2019).

Andreux et al., "The mitophagy activator urolithin A is safe and induces a molecular signature of improved mitochondrial and cellular health in humans," Nature Metabolism, 1:595-603 (2019).

Bai et al., "Active Compounds from Lagerstroemia speciosa, Insulin-like Glucose Uptake-Stimulatory/Inhibitory and Adipocyte Differentiation-Inhibitory Activities in 3T3-L1 Cells," J Agric Food Chem, 56(24):11668-11674 (2008).

Basu et al., "Pomegranate juice: A heart-healthy fruit juice," Nutr Rev, 67(1): 49-56 (2009).

Berry Health Benefits Symposium (2009 Berry Health Benefis Symposium).

Bhattacharyya et al., "Beneficial Effect of Processed Shilajit on Swimming Exercise Induced Impaired Energy Status of Mice," Pharmacologyonline, 1: 817-825 (2009).

Bhattacharyya et al., "Shilajit Dibezno-alpha-Pyrones: Mitochondria Targeted Antioxidants," Pharmacologyonline, 2: 690-698 (2009).

Bialonska, et al., "Urolithins, Intenstinal Microbial Metabolites of Pomegranate Ellagitannins, Exhibit Potent Antioxidant Activity in a Cell-Based Assay," J Agric Food Chem, 57(21); 10181-10186, 2009.

Bishayee, "Cancer prevention and treatment with resveratrol: from rodent studies to clinical trials." Cancer Prevention Research 2(5) (2009): 409-418.

Bishop et al., "Neural mechanisms of ageing and cognitive decline," Nature, 464(7288):529-535 (2010).

Brummer et al., "Particle Characterisation in Excipients, Drug Products and Drug Substances" SGS Life Science Services, Issue 11: 6 pages (2008).

Cerda et al., "Identification of Urolithin A as a metabolite produced by human colon microflora from ellagic acid and related compounds," J Agric Food Chem, 53(14): 5571-5576 (2005).

Cerda et al., "Pomegranate juice supplementation in a chronic obstructive pulmonary disease: a 5-week, randomized, double-blind, placebo-controlled trial," Eur J Clin Nutr, 60: 245-253 (2006).

Cerda et al., "Repeated oral administration of high doses of the pomegranate ellagitannin punialagin to rats for 37 days is not toxic," J. Agric. Food Chem., 51(11):3493-3501 (2003).

Chaudhary et al., "Enhancement of solubilization and bioavailability of poorly soluble drugs by physical and chemical modifications: A recent review," Journal of Advanced Pharmacy Education & Research, 2(1):32-67 (2012).

Chen et al., "Coordination of Autophagy and the Proteasome in Resolving Endoplasmic Reticulum Stress," Veterinary Pathology 48(1):245-253 (2011).

Chen et al., "Resveratrol ameliorates metabolic disorders and muscle wasting in streptozotocin-induced diabetic rats," American Journal of Physiology Endocrinology and Metabolism 301.5 (2011): E853-E863.

Chen, T. et al., "Rapamycin and other longevity-promoting compounds enhance the generation of mouse induced pluripotent stem cells", Aging Cell, 10(5):908-911 (Anatomical Society of Great Britain and Ireland, UK, Jun. 14, 2011).

Cintamani, "Dadima (anara) Guna" Gangavishnu Shrikrishan Das, 170 (1937).

Curto et al., "Inhibitors of mammalian melanocyte tyrosinase: in vitro comparisons of alkyl esters of gentisic acid with other putative inhibitors," Biochem Pharmacol, 57:663-672 (1999).

De Meyer et al., "Autophagy in the cardiovascular system," Biochimica et Biophysica Acta 1793: pp. 1485-1495 (2009).

Dell'agli, et al., "Ellagitannins of fruit rind of pomegranate (*Punica granatum*) antagonize in vitro the host inflammatory response mechanism involved in the onset of malaria," Malaria J, 9: 208 (2010).

Du et al., "Starving Neurons Show Sex Difference in Autophagy," The Journal of Biological Chemistry, 284(4): 2383-2396 (2009).

Eisenberg et al., "Induction of autophagy by spermidine promotes longevity." Nature Cell Biology 11(11) (2009): 1305-1314.

Ertam et al., "Efficiency of ellagic acid and arbutin in melasma: A randomized, prospective, open-label study," Journal of Dermatology, 35: 570-574 (2008).

Esmaillzadeh et al., "Concentrated pomegranate juice improves lipid profiles in diabetic patients with hyperlipidemia," J Med Food, 7(3): 305-308 (2004).

Espin et al., "Iberian pig as a model to clarify obscure points in the bioavailability and metabolism of ellagitannins in humans," J Agric Food Chem, 55(25): 10476-10485 (2007).

Extended European Search Report for EP Application No. 18166896.3 dated Jun. 6, 2018.

Extended European Search Report for EP Application No. 18166897.1 dated May 28, 2018.

Extended European Search Report for EP Application No. 23175506.7 dated Jan. 8, 2023.

Farris, "The anti-aging effects of niacinamide" Dermatology Times, [online] Oct. 14, 2015<https://www.dermatologytimes.com/view/anti-aging-effects-niacinamide>.

Friedman et al., "NSAIDs in Dermatologic Therapy: Review and Preview." J Cutan Med Surg 2002, 6(5):449-59.

Ghosal et al., "Effects of shilajit and its active constituents on learning and memory in rats," Phytotherapy Res, 7(1): 29-34 (1993).

Ghosal et al., "Shilajit. Part 4. Chemistry of Two Bioactive Benzopyrone Metabolites," J Chem Research (S), 11: 350-351 (1989).

Gimenez-Bastida et al., "Ellagitannin metabolites, urolithin A glucuronide and its aglycone urolithin A, ameliorate TNF-induced inflammation and associated molecular markers in human aortic endothelial cells," Mol. Nutr. Food. Res. 56(5): 784-796 (2012).

Gonzalez-Sarrias et al., "Dissimilar In Vitro and In Vivo Effects of Ellagic Acid and Its Microbiota-Derived Metabolites, Urolithins, on the Cytochrome P450 1A1," Journal of Agricultural and Food Chemistry, 57: 5623-5632 (2009).

Gonzalez-Sarrias et al., "NF-? B-dependent anti-inflammatory activity of urolithins, gut microbiota ellagic acid-derived metabolites, in human colonic fibroblasts." British Journal of Nutrition 2010, 104, 503-512.

Gulcin et al., "Antioxidant and Antiradical Activities of L-carnitine," Life Sciences, 78: 803-811 (2006).

Hartman et al., "Pomegranate juice decreases amyloid load and improves behavior in a mouse model of Alzheimer's disease", Neurobiology of Disease, 24(3):506-515 (Elsevier Inc., St. Louis, MO 2006).

Hipkiss, "Aging, proteotoxicity, mitochondria, glycation, NAD+ and carnosine: possible inter-relationships and resolution of the oxygen paradox", Frontiers in aging neuroscience: 10 (2010).

Hoefer et al., "Fear conditioning in frontotemporal lobar degeneration and Alzheimer's disease," Brain, 131: 1646-1657 (2008).

Hu et al., "Efficacy and comparative effectiveness of sirolimus as an anticancer drug." The Laryngoscope 121(5) (2011): 978-982.

(56) References Cited

OTHER PUBLICATIONS

Ibn-e-Sina, "Halelah" Institute of History of Medicine and Medical Research, 409-410 (1987).
IN Application No. 392/CHE/2004 A (DSM IP Assets BV [NL]), filed Apr. 28, 2004.
International Search Report and Written Opinion for International Application No. PCT/EP24/80149 dated Jan. 29, 2025.
International Search Report and Written Opinion for International Application No. PCT/US11/67229 dated Jul. 25, 2024.
International Search Report and Written Opinion for International Application No. PCT/US13/48310 dated Jan. 22, 2014.
Ishimoto H. et al., "In vivo anti-inflammatory and antioxidant properties of ellagitannin metabolite urolithin A." Bioorg Med Chem Lett, 21(19): 5901-5904 (2011).
Islam et al. "Biotransformation of 3-hydroxydibenzo-a-pyrone into 3, 8 dihydroxydibenzo-a-pyrone and aminoacyl conjugates by Aspergillus niger isolated from native "shilajit"." Electronic Journal of Biotechnology 11.3 (2008): 1-10.
Johanningsmeier et al., "Pomegranate as a functional food and nutraceutical source," Ann Rev Food Sci Technol, 2:181-201 (2010).
Kaarniranta et al., "Age-Related Macular Degeneration (AMD): Alzheimer's Diesease in the Eye?," Journal of Alzheimer's Disease, 24(4):615-631 (2011).
Kabiruddin, "Rubb-e- Anaar Sheerin" Daftar-al-Maseeh, 75 (1938).
Kasimsetty, et al., "Colon cancer chemopreventive activities of pomegranate ellagitannins and Urolithins," J Agric Food Chem, 58(4): 2180-2187 (2010).
Kharkevich, "Parmakolociva" [Pharmacology], Manual for Students of Medical Institutes, Moscow, Meditsina, 47-48 (1987).
Kiss et al., "Epigenetic modulation of mechanisms involved in inflammation: Influence of selected polyphenolic substances on histone acetylation state", Food Chemistry, 131(3):1015-1020 (Elsevier Ltd., Netherlands, Sep. 26, 2011).
Landete, "Ellagitannins, ellagic acid and their derived metabolites: A review about source, metabolism, functions and health", Food Research International, 44(5):1150-1160 (Elsevier Applied Science, Barking, GB, Apr. 17, 2011).
Larrosa et al., "Anti-inflammatory properties of a pomegranate extract and its metabolite urolithin-A in a colitis rat model and the effect of colon inflammation on phenolic metabolism", Journal of Nutritional Biochemistry, 21:717-725 (Elsevier Inc., 2010).
Larrosa et al., "Ellagitannins, ellagic acid and vascular health", Molecular Aspects of Medicine, 31(6):513-539 (Pergamon Press, Oxford, Great Britain, Dec. 1, 2010).
Lee et al., "b-Secretase (BACE1) Inhibitors from Sanguisorbae Radix", Arch. Pharm. Res., 28(7):799-803 (Korea, 2005).
Lin et al., "Pharmacological Promotion of Autophagy Alleviates Steatosis and Injury in Alcoholic and Non-alcoholic Fatty Liver Conditions in Mice," J Hepatol. May 2013; 58(5):993-999.
Liu et al. "Antiaging effects of urolithin A on replicative senescent human skin fibroblasts", Rejuvenation Research, 22(3): 191-200 (2019).
Liu et al., "Appendix C: Impact of Urolithin A vs Placebo Supplementation on Muscle Endurance and Mitochondrial Health in the Elderly: A Randomized Clinical Trial," Manuscript Draft.
Liu et al., "Chemical constituents of Panax ginseng and Panax notoginseng explain why they differ in therapeutic efficacy." Pharmacological Research 161 (2020): 105263.
Majoosi, "Rubb-e-Rumman" Central Council for Research in Unani Medicine, 591 (2005).
Manach et al., "Bioavailability and bioefficacy of polyphenols in humans. I. Review of 97 bioavailability studies 1-3," Am. J. Clin. Nutr. 81(suppl):230S-242S (2005).
Markaki et al., "Modeling human diseases in Caenorhabditis elegans," Biotechnol J, 5:1261-1276 (2010).
Mingorance et al., "Critical update for the clinical use of L-carnitine analogs in cardiometabolic disorders," Vascular Health and Risk Management, 7:169-176 (2011).
National Institute of Mental Health, "I'm So Stressed Out!" Fact Sheet, 2023, retrieved from https://www.nimh.nih.gov/sites/default/files/documents/health/publications/so-stressed-out-fact-sheet/Im-So-Stressed-Out.pdf, 2 pages.
Ndiaye et al., "The grape antioxidant resveratrol for skin disorders: promise, prospects, and challenges." Arch Biochem Biophys 2011, 508(2) 164-170.
Nih, "What Is Atherosclerosis?" NHLBI, National Institutes of Health (2016).
Nolan et al., "Over-the-Counter Topical Skincare Products: A Review of the Literature." Journal of Drugs in Dermatology, 2012, 11(2), 220-224.
Pandya et al., "Disorders of Hyperpigmentation," New and Emerging Therapies, 18(1):91-98 (2000).
Park et al., "Micronization of arbutine using supercritical anti-solvent," Korean Journal of Chemical Engineering, 25(3): 581-584 (2008).
Partial European Search Report for European Application No. 17186188.3 dated Oct. 27, 2017.
Paula's choice skincare, "Trehalose", [online] https://www.paulaschoice.com/ingredients/ingredient-trehalose.html [Accessed Aug. 11, 2022].
Percival, "Antioxidants," Clinical Nurtition Insights, 1998.
Puzzo et al., "Behavioral assays with mouse models of Alzheimer's disease: practical considerations and guidelines," Biochemical Pharmacology, 88(4): 46 pages (2014).
Ratnam et al., "The co-encapsulated antioxidant nanoparticles of ellagic acid and coenzyme Q10 ameliorates hyperlipidemia in high fat diet fed rats," Journal of Nanoscience and Nanotechnology 9 (2009): 6741-6746.
Raza et al., "Effect of Bitter Melon (*Momordica charantia*) Fruit Juice on the Hepatic Cytochrome P450-Dependent Monooxygenases and Glutathione S-Transferases in Streptozotocin-Induced Diabetic Rats," Biochemical Pharmacology, 52: 1639-1642 (1996).
Raza et al., "Modulation of Xenobiotic Metabolism and Oxidative Stress in Chronic Streptozotocin-Induced Diabetic Rats Fed with Momordica charantia Fruit Extract," J Biochem Molecular Toxicology, 14(3): 131-139 (2000).
Reuter et al., "Carnitine and Acylcarnitines Pharmacokinetic, Pharmacological and Clinical Aspects," Clin Pharmacokinet, 51 (9): 553-572 (2012).
Rock et al., "Consumption of wonderful variety pomegranate juice and extract by diabetic patients increases paraoxonase 1 association with high-density lipoprotein and stimulates its catalytic activities," J Agric Food Chem, 56(18): 8704-8713 (2008).
Rubinsztein et al., "Autophagy and aging", Cell 146(5): 682-695 (2011).
Ryu et al., "Urolithin A induces mitophagy and prolongs lifespan in C. elegans and increases muscle function in rodents" Nature Medicine, vol. 22, No. 8 (2016).
Sanders et al., "The place of the hippocampus in fear conditioning," European Journal of Pharmacology, 463: 217-223 (2003).
Sarasamgrahah, "Anara Sarbata" Shri Baidyanath Ayurveda Bhavan Limited, 569 (2003).
Sastre et al., "The role of mitochondrial oxidative stress in aging", 2003, Free Radio Biol Med, 35: 1-8.
Saul et al., "Diversity of Polyphenol Action in Caenohabditis elegans: Between Toxicity and Longevity", Journal of Natural Products, 74(8):1713-1720 (American Chemical Society and American Society of Pharmacognosy, USA, Aug. 26, 2011).
Search Report for GB Application No. 2308224, dated Nov. 27, 2023.
Search Report for GB Application No. 2316295.1 dated Apr. 18, 2024.
Seeram et al., "Pomegranate Ellagitannin-Derived Metabolites Inhibit Prostate Cancer Growth and Localize to the Mouse Prostate Gland", J. Agric. Food Chem., 55:7732-7737 (American Chemcal Society, USA, 2007).
Silverman et al., "Modeling molecular and cellular aspects of human disease using the nematode caenorhabditis elegans," Pediatric Research, 65(1):10-18 (2009).
Singh et al., "Appendix B: Urolithin A improves leg muscle strength, exercise performance and mitochondrial health in a proof-of-concept clinical trial in overweight adults," Manuscript Draft.

(56) References Cited

OTHER PUBLICATIONS

Song et al., "Metformin kills and radiosensitizes cancer cells and preferentially kills cancer stem cells." Scientific Reports 2 (2012): 362.
Sorgen, "Eat Smart for a Healthier Brain," WebMD, accessed online:https://www.webmd.com/diet/features/eat-smart-healthier-brain?print=true.
Stout et al., "Mitochondria's Role in Skin Ageing," Biology, 8(29): 12 pages (2019).
Sumner et al., "Effects of pomegranate juice consumption on myocardial perfusion in patients with coronary heart disease," Am J Cardiol, 96(6): 810-814 (2005).
Taylor et al., "Behavioral phenotyping of mouse models of Parkinson's Disease," Behavioural Brain Research, 211(1): 19 pages (2010).
Third Party Observation for Application No. EP20180166897, dated Apr. 8, 2024.
Trombold et al., "Ellagitannin Consumption Improves Strength Recovery 2-3 d after Eccentric Exercise", Medicine and Science in Sports and Exercise, 42:493-498 (American College of Sports Medicine, Mar. 2010).
Uchida, "Pathologic Changes and Autophagy: New Insights for the Pathogenesis of Animal Diseases," Veterinary Pathology 54(6):881-884 (2017).
Verzelloni et al., "Antiglycative and Neuroprotective Activity of Colon-Derived Polyphenol Catabolites" Molecular Nutrition and Food Research, 55(1): S35-S43 (2011).
Verzelloni et al., "Antiglycative and neuroprotective activity of colonderived polyphenol catabolites." Mol. Nutr. Food Res, 55(1):35-43 (2011).
Viuda-Martos et al., "Pomegranate and its Many Functional Components as Related to Human Health: A Review", Comprehensive Reviews in Food Science and Food Safety, 9(6):635-654 (Oct. 22, 2010).
Wang et al., "Antimelanogenic Effect of Urolithin A and Urolithin B, the Colonie Metabolites of Ellagic Acid, in B16 Melanoma Cells" Journal of Agricultural and Food Chemistry, 65: 6870-6876 (2017).
Wang et al., "Gut microbial transformation, a potential improving factor in the therapeutic activities of four groups of natural compounds isolated from herbal medicines." Fitoterapia 138 (2019): 104293.
Zenjun et al., "Distribution of Ellagic Acids in Plantae and Thier Bioactivies," Natural Product Research and Development, 22:519-524 and 540 (2010).
Zihong, "Practical Family Nutrition," Wuhan University Press, p. 251 (2021).

* cited by examiner

UROLITHIN GUMMY (PECTIN) FORMULATIONS

RELATED APPLICATION

This application is a continuation of U.S. patent application Ser. No. 18/680,751, filed May 31, 2024, which claims the benefit of priority to GB Patent Application No. 2308224.1, filed June 1,2023.

BACKGROUND

Urolithins have been proposed as treatments for a variety of conditions related to inadequate mitochondrial activity, including obesity, reduced metabolic rate, metabolic syndrome, diabetes mellitus, cardiovascular disease, hyperlipidaemia, neurodegenerative diseases, cognitive disorders, mood disorders, stress, and anxiety disorders; for weight management, or to increase muscle performance or mental performance. See WO2012/088519 (Amazentis SA). In WO2007/127263 (The Regents of the University of California), the use of urolithins for the treatment of various neoplastic diseases is described.

International patent publication WO2014/004902 (derived from application PCT/US2013/48310) discloses a method of increasing autophagy, including specifically mitophagy, in a cell, comprising contacting a cell with an effective amount of a urolithin or a pharmaceutically acceptable salt thereof, thereby increasing autophagy, including specifically mitophagy, in the cell. Administration may be to a subject having a disease or condition selected from metabolic stress, cardiovascular disease, endothelial cell dysfunction, sarcopenia, muscle degenerative disease, Duchenne muscular dystrophy, alcoholic liver disease, non-alcoholic fatty liver disease, drug-induced liver or muscle injury, a1-antitrypsin deficiency, ischemia/reperfusion injury, inflammation, aging of the skin, inflammatory bowel disease, Crohn's disease, obesity, metabolic syndrome, type II diabetes mellitus, hyperlipidaemia, osteoarthritis, neurodegenerative disease, Alzheimer's disease, Huntington's disease, Parkinson's disease, amyotrophic lateral sclerosis, age-related macular degeneration, mitochondrial diseases (including for example poor growth, loss of muscle coordination, muscle weakness, visual problems, hearing problems, heart disease, liver disease, kidney disease, gastrointestinal disorders, respiratory disorders, neurological problems, autonomic dysfunction sometimes learning disabilities, and dementia (as a result of mitochondrial disease), muscle diseases; cancer, cognitive disorder, stress, and mood disorder.

Chewable products (gummy formulations), generally made of a gelatine or a pectin matrix with sugar, glucose, corn syrup, flavouring, colouring and citric acid have been a popular snack food product. The product (formulation) typically has a gel or gel-like structure and texture, and is produced in a variety of shapes, colours and flavours that are chewable when consumed. Recently, gummy products have been supplemented with vitamins, minerals, essential oils and other nutritional supplements to provide a nutritional supplement that appeals to children and adults that do not like to swallow or have difficulty swallowing tablets or capsules. Gelatine is a soluble and gelatinous protein that is extracted from animal bones, skin, tendons and muscles, and then partially hydrolyzed by acid, alkali or enzymes. Gelatine has been extensively used in chewable formulations, however, more recently there has been a decrease in use of gelatine. This has been advocated due to its animal origin, since traditionally, vegetarian consumers and their religious advocate of avoiding animal-derived products. More recently, although ordinary consumers do not concern vegetarianism or religious preferences, they also tend to prefer foods in which gelatine is replaced with another agent, for instance gums extracted from plants, for example, pectin.

However, although plant-based chewable formulations, such as formulations, comprising pectin, are a popular option they can be difficult to manufacture. Therefore, there is an on-going need for improvements in chewable formulations comprising pectin, especially to formulate novel active ingredients as chewable formulations.

SUMMARY

The invention relates to composition of urolithins comprising urolithins and pectin and formulations of urolithins, specifically chewable formulations, comprising urolithins and a gelling agent. The invention further comprises compositions and chewable formulations comprising urolithins in combination with other active ingredients and processes for the preparation of such compositions and formulations. The invention further comprises methods of using such compositions and formulations in the treatment of conditions and diseases and for the promotion of health and performance, such in the improving muscle function. One aspect of the invention provides a composition comprising:

(a) a compound of formula (I) or a salt thereof:

(I)

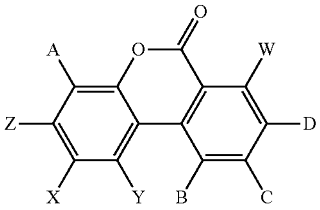

wherein:

A, B, C and D are each independently selected from H and OH;

W, X and Y are each independently selected from H and OH; and

Z is selected from H and OH; and (b) pectin.

In some embodiments, the pectin is selected from low methoxy pectin, high methoxy pectin or amidated low methoxy-pectin, or a mixture thereof, for example, wherein the pectin is high methoxypectin.

In some embodiments, the compound of Formula (I) and pectin are in the ratio 1 to about 1 to 1 to about 10 (w/w).

In some embodiments the composition is a gummy.

In some embodiments the composition is a powder.

In some embodiments the composition is a mixture.

In some embodiments the composition is prepared by spray dring.

In some embodiments the compound of Formula (I) is in amorphous form or partially in amorphous form.

In some embodiments, when dependent on claim 7, wherein the composition is prepared by spray-drying in a solvent selected from: ethanol and water.

In some embodiments, the composition further comprising one or more of the following:

a). soluble fibre, for example, soluble tapioca fibre;

b). a low calorie sweetener, for example, allulose; and c). citric acid and/or a citrate salt (for example, sodium citrate), for example, citric acid and a salt of citric acid (for example, sodium citrate).

In some embodiments, the composition comprising:

a). about 5% to about 20% (w/w) of a compound of formula (I); for example, urolithin A; and b). about 0.5% to about 4% (w/w) pectin;

and further comprising one or more of the following c). about 25% to about 45% (w/w) soluble fibre, for example, soluble tapioca fibre;

d). about 25% to about 45% (w/w) of a low calorie sweetener, for example, allulose; and e). about 0.5% to about 4% (w/w) citric acid and/or a citrate salt (for example, sodium citrate), for example, citric acid and a salt of citric acid (for example, sodium citrate).

In some embodiments, a chewable formulation comprising:

a) a gelling component, b) a compound of formula (I) or a salt thereof:

(I)

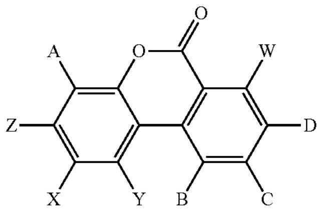

wherein:

A, B, C and D are each independently selected from H and OH;

W, X and Y are each independently selected from H and OH; and

Z is selected from H and OH.

In some embodiments, the chewable formulation further comprising:

c) a sweetener system, for example, wherein the sweetener system comprises one or more sweeteners.

In some embodiments, the gelling component comprises one or more of the following: pectin, gelatine, and modified starch.

In some embodiments, the gelling component comprises pectin, for example, high methoxy pectin.

In some embodiments, the high methoxy pectin has an esterification range of about 50% to about 75%.

In some embodiments, the formulation comprises about 0.5% to about 5% (w/w) gelling component, for example about 0.5% to about 4% (w/w) pectin, such as about 1.5% to about 3% (w/w) pectin.

In some embodiments, the composition further comprising:

d) a fibre component, for example, a soluble fibre component.

In some embodiments, the fibre component is selected from: soluble tapioca, *psyllium* husk powder, apple fibre or mixtures thereof.

In some embodiments, the formulation has a brix between about 75 degrees to about 85 degrees.

In some embodiments, the formulation has a terminal boiling point between about 108° C. to about 111° C.

In some embodiments, the formulation comprises less than about 30% (w/w) sugar.

In some embodiments, the compound of Formula (I) is selected from urolithin A, urolithin B, urolithin C or urolithin D, for example, urolithin A In some embodiments, the compound of formula (I), for example, urolithin A, is present in the range 100 mg to 2500 mg.

In some embodiments, the composition or formulation as disclosed herein for use as a medicament, dietary supplement, functional food or medical food.

In some embodiments, the composition or formulation as disclosed herein for use in the treatment and/or prophylaxis of a muscle-related pathological condition, for example, wherein the muscle-related pathological condition is selected from musculoskeletal diseases or disorders; muscle wasting; myopathies; neuromuscular diseases, such as Duchenne muscular dystrophy and other dystrophies; sarcopenia, for example, acute sarcopenia; muscle atrophy and/or cachexia.

In some embodiments, a method of enhancing muscle performance, of improving endurance capacity, or of improving, maintaining or reducing the loss of muscle function comprising administering to a subject an effective amount of a composition or formulation as disclosed herein, for example, wherein the subject suffers age-related decline in muscle function, age-related sarcopenia, age-related muscle wasting, physical fatigue, muscle fatigue, and/or is frail or pre-frail.

In some embodiments, the use of a composition or formulation as disclosed herein in a method of improving physical performance, for example, wherein the improvement in physical performance is in a healthy individual or in the elderly.

In some embodiments, the use of a composition or chewable formulation as disclosed herein in a method of increasing muscle strength, increasing or maintaining muscle mass or improving muscle recovery.

In some embodiments, the use of a composition or chewable formulation as disclosed herein in a method of improving physical endurance.

In some embodiments, the use of a composition or chewable formulation as disclosed herein in a method of inhibiting or retarding physical fatigue, enhancing working capacity and endurance, reducing muscle fatigue, enhancing cardiac and cardiovascular function.

In some embodiments, the use of a composition or chewable formulation as disclosed herein in a method of enhancing sports performance.

In some embodiments, the use of a composition or chewable formulation as disclosed herein for improving non-disease health conditions characterised by inadequate mitochondrial activity.

In some embodiments, the composition or chewable formulation as disclosed herein for use in treating disease conditions characterised by inadequate mitochondrial activity.

In some embodiments, a composition or chewable formulation as disclosed herein for enhancing healthspan.

DETAILED DESCRIPTION

Figure 1:
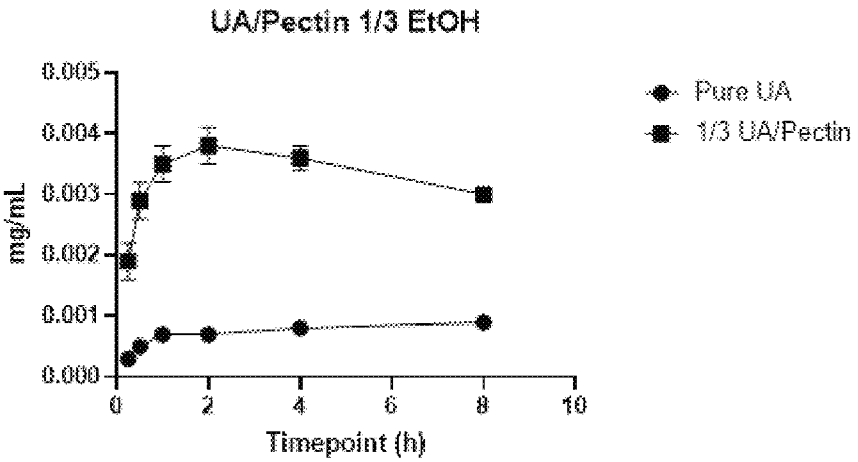
FIG. 1: Dissolution profiles of powders containing 10 mg UA complexed with Citrus pectin in FaSSIF medium compared to 10 mg of pure UA powder, using EtOH as solvent. Left graph: comparison of a formulation UA/Pectin in which excipients are in a w/w ratio of 1/1. Right graph: comparison of a formulation UA/Pectin in which excipients are in a w/w ratio of 4/1.
Figure 1:
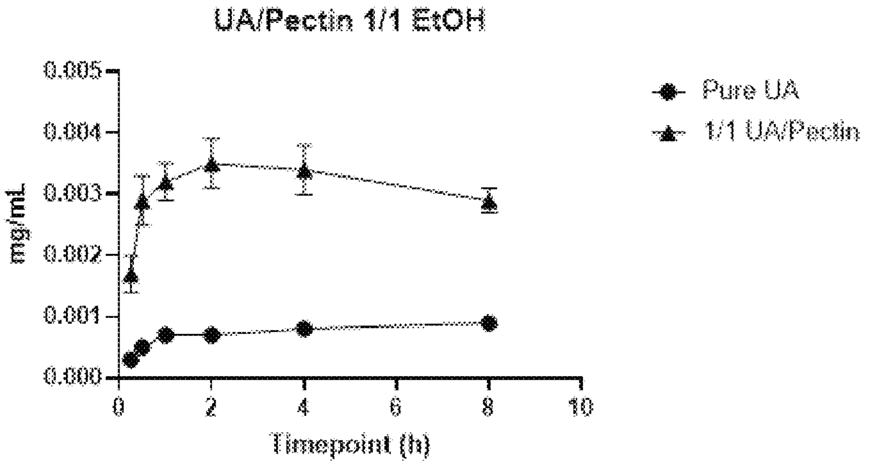

According to a one aspect of the invention there is provided a chewable formulation comprising:

a) a gelling component, and b) a compound of formula (I) or a salt thereof:

(I)

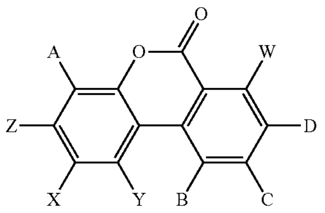

wherein:

A, B, C and D are each independently selected from H and OH;

W, X and Y are each independently selected from H and OH; and

Z is selected from H and OH.

According to a further aspect of the invention, there is provided a chewable formulation, comprising:

a) a gelling component, b) a compound of formula (I) or a salt thereof:

wherein the formulation does not include a sweetener system.

According to a further aspect of the invention, there is provided a chewable formulation, comprising:

a) a gelling component, b) a compound of formula (I) or a salt thereof:

c) a sweetener system, wherein the sweetener system comprises one or more artificial sweeteners.

According to a further aspect of the invention, there is provided a chewable formulation, comprising:

a) a gelling component, b) a compound of formula (I) or a salt thereof:

c) a sweetener system, wherein the sweetener system comprises allulose.

According to a further aspect of the invention, there is provided a chewable formulation, comprising:

a) a gelling component, b) a compound of formula (I) or a salt thereof:

c) a sweetener system, wherein the sweetener system comprises inulin.

According to a further aspect of the invention, there is provided a chewable formulation, comprising:

a) a gelling component, b) a compound of formula (I) or a salt thereof:

c) a sweetener system, wherein the sweetener system consists of one or more artificial sweeteners.

According to a further aspect of the invention, there is provided a chewable formulation, comprising:

a) a gelling component, b) a compound of formula (I) or a salt thereof, and c) a pH buffer.

According to a further aspect of the invention, there is provided a chewable formulation, comprising:

a) a gelling component, b) a compound of formula (I) or a salt thereof, and c) a pH between about 2.7 and about 3.7.

According to a further aspect of the invention, there is provided a chewable formulation, comprising:

a) a gelling component, b) a compound of formula (I) or a salt thereof, and c) a pH buffer, wherein the pH buffer maintains the pH between about 2.7 and about 3.7.

According to a further aspect of the invention, there is provided a chewable formulation, comprising:

a) a gelling component, b) a compound of formula (I) or a salt thereof, and c) a pH between about 2.7 and about 4.0.

According to a further aspect of the invention, there is provided a chewable formulation, comprising:

a) a gelling component, b) a compound of formula (I) or a salt thereof, and c) a pH buffer, wherein the pH buffer maintains the pH between about 2.7 and about 4.0.

According to a further aspect of the invention, there is provided a chewable formulation, comprising:

a) a gelling component, b) a compound of formula (I) or a salt thereof, and c) a fibre component, such as a soluble fibre component.

According to a further aspect of the invention, there is provided a chewable formulation, comprising:

a) a gelling component, b) a compound of formula (I) or a salt thereof, and c) a brix between about 75 degrees to about 85 degrees for example, about 77 degrees to about 82 degrees.

According to a further aspect of the invention, there is provided a chewable formulation, comprising:

a) a gelling component, b) a compound of formula (I) or a salt thereof, and c) a terminal boiling point between about 108° C. and about 111° C. (about 228° F. to about 231° F.).

According to a further aspect of the invention, there is provided a low-calorie chewable formulation, comprising:

a) a gelling component, b) a compound of formula (I) or a salt thereof, and wherein the formulation comprises less than about 30% (w/w) sugar.

According to a further aspect of the invention, there is provided a low-calorie chewable formulation, comprising:

a) a gelling component, b) a compound of formula (I) or a salt thereof, and wherein the formulation comprises less than about 50% (w/w) sugar, for example less than about 45% (w/w) sugar, such as less than about 40% (w/w) or less than about 30% (w/w) sugar.

According to a further aspect of the invention, there is provided a low-calorie chewable formulation, comprising:

a) a gelling component, b) a compound of formula (I) or a salt thereof, and wherein the formulation comprises about 25% to about 40% sugar.

According to a further aspect of the invention, there is provided a chewable formulation, comprising:

a) a gelling component, b) a compound of formula (I) or a salt thereof, and c) wherein the gelling component comprises pectin with an esterification range of about 55% to about 75%, for example, 60% to about 68%.

According to a further aspect of the invention, there is provided a chewable formulation, comprising:

a) a gelling component, comprising a high-methoxy pectin, and b) a compound of formula (I) or a salt thereof.

According to a further aspect of the invention, there is provided a chewable formulation, comprising:

a) a gelling component, comprising a low-methoxy pectin, and b) a compound of formula (I) or a salt thereof.

According to a further aspect of the invention, there is provided a chewable formulation, comprising:

a) a gelling component, comprising an amidated low-methoxy pectin, and b) a compound of formula (I) or a salt thereof.

According to a further aspect of the invention, there is provided a chewable formulation, comprising:

a) a gelling component, comprising a low-methoxy pectin, b) a compound of formula (I) or a salt thereof, and c) a divalent cation, for example, provided by a calcium salt, such a calcium salt selected from calcium chloride, calcium citrate and/or calcium sulphate.

In one embodiment, the formulation comprises a calcium salt in the range of about 0.05% to about 0.1% (w/w).

A suitable gelling component is one which provides a cohesive gelled product, when used alone or used with other gelling components. A gelling component may be selected from one of more gelling agents. For example a gelling agent selected from pectin, gelatine, and modified starch. In one embodiment the gelling agent is selected from: pectin and gelatine. In a further embodiment the gelling agent comprises pectin and gelatine. In a further embodiment the gelling agent comprises pectin. In a further embodiment, the gelling component is pectin. In a further embodiment, the gelling agent comprises gellan and carrageenan.

In a further embodiment, the formulation comprises about 0.5% to about 5% (w/w) gelling component.

In a further embodiment, the formulation comprises about 0.5% to about 4% (w/w) pectin, such as about 0.5% to about 5% (w/w), about 0.5% to about 4%, about 1.5% to about 3% (w/w) pectin, such as about 1% to about 2% (w/w), such as about 1.2% to about 1.8% (w/w), such as about 1.4% (w/w), such as about 1.5% (w/w), such as about 1.6% (w/w), such as about 1.7% (w/w).

In one embodiment, the formulation is essentially free of animal-derived products, for example, essentially free of gelatine.

In a further embodiment, the gelling component is selected from one or more of: carrageenan, alginic acid, sodium alginate, xanthan gum, gellan gum, gum Arabic, guar, and locust bean gum.

In a further embodiment, the gelling agent is selected from one or more of: pectin and gelatine.

In one embodiment, the formulation comprises a gelling component comprising pectin. In a further embodiment, the formulation comprises a gelling component consisting of pectin.

A pectin suitable for formulations of the invention is any pectin which provides the necessary gel strength for formulations of the invention. In one embodiment of the invention, the pectin is a high methoxy pectin. A high methoxy pectin is one wherein at least 50% of the galacturonic acid units are esterified with a methoxy group.

In one embodiment the methoxy pectin is esterified in a range of about 50% to about 75%, for example, about 55% to about 75%, about 55% to about 70%, or about 65% to about 75% methoxypectin. In a further embodiment the esterification range is about 60% to about 68%. In a further embodiment the esterification range is about 63% to about 65%. In a further embodiment, the methoxy pectin is about 55% esterified, about 60% esterified, about 65% esterified or about 70% esterified.

In a further embodiment of the invention, the pectin is a low methoxy pectin. A low methoxy pectin is one wherein less than 50% of the galacturonic acid units are esterified with a methoxy group.

Formulations of the invention may further comprise fibre. In one embodiment, a naturally derived fibre is used, for example, one or more selected from naturally derived inulin, inulin extract, synthetic inulin, hydrolysis products of inulin commonly known as fructooligosaccharides, galacto-oligosaccharides, xylooligosaccharides, oligo derivatives of starch, husks, brans, *psyllium*, polysaccharides, polycarbophil, lignin, arabinogalactans, chitosans, oat fibre, soluble corn fibre, non-digestible corn dextrin, non-digestible wheat dextrin, locust bean gum and derivatives of locust bean gum, hydroxypropylmethyl cellulose (HPMC), pectin, and mixtures thereof.

In some embodiments, fibre may include inulin, wheat dextrin, or fructooligosaccharides. Inulin, wheat dextrin, and fructooligosaccharides may also act as a thickening agent and improve the texture of the formulation. Various load rates of dietary fibre can be incorporated in the formulation to create improved texture and at certain load rates can provide dietary benefits including promoting a healthy digestion system, controlling blood sugar levels, and providing probiotic benefits. The addition of the dietary fibre along with the remaining components allow for the addition of water that helps displace sugar within the flavoured chewy or gummy confection.

In a further embodiment the fibre is selection from soluble tapioca, *psyllium* husk powder, apple fibre, dextrins, inulin, or mixtures thereof.

In one embodiment, the fibre may present in an amount of from about 10% to about 60% (w/w), alternatively about 20% to about 60% (w/w), alternatively about 30% to about 60% (w/w), alternatively about 30% to about 50% (w/w), alternatively about 30% to about 40%, such as about 35% (w/w), such as about 37% (w/w), such as about 40% (w/w).

Conventional chewable formulations comprise no more than 6% (w/w) of active ingredients. However, through careful selection of active ingredients, formulations of the invention can comprise more than about 20% (w/w) active ingredients. In some embodiments, the formulation may include the active component from about 5% to about 25%, (w/w) active ingredients, for example, about 6% to about 25% (w/w) active ingredients, for example, about 10% to about 25% (w/w) active ingredients, for example, about 15% to about 25% (w/w) active ingredients, for example, about 10% to about 20% (w/w) or about 6% to about 20%, active ingredients, for example, about 20% (w/w) active ingredients.

In one embodiment, the chewable formulations of the invention have reduced sugar content when compared to conventional commercially available chewable formulations. For example, chewable formulations of the invention comprising less than about 70% (w/w) sugar, for example, less than about 60% (w/w), for example, less than about 50% (w/w), for example, less than about 40% (w/w), for example, less than about 30% (w/w) for example, less than about 25% sugar, such as less than about 20% (w/w), less than about 15% sugar, less than about 10%, less than about 5% or about 0% sugar,.

In one embodiment, formulations of the invention further comprise an additive selected from sweeteners, food acids, flavouring agents, colouring agents, humectants, bulking agents, fatty acids, triglycerides, plasticizers, emulsifiers, thickeners, preservatives, and/or a mixture thereof. In a further embodiment, formulations of the invention comprise and additive selected from: sweeteners, food acids, flavouring agents, and colouring agents.

Sweeteners

In general, an effective amount of sweetener may be utilized to provide the level of sweetness desired, and this amount may vary with the sweetener selected. Sweeteners may include one or more monosaccharides or disaccharides. Examples include sugar, sucrose, invert sugar, dextrose, lactose, honey, malt syrup, malt syrup solids, maltose, fructose, granular fructose, maple syrup, rice syrup, rice syrup solids, sorghum syrup, refiners syrup, corn syrup, corn syrup solids, high fructose corn syrup, molasses, or combinations thereof.

In one embodiment, the sweetener includes common sugars such as sucrose and glucose, polyols such as maltitol, erythritol, and isomalt, syrup sweeteners such as glucose syrup, corn syrup, high fructose corn syrup, and juice concentrates. In a further embodiment, the sweetener includes allulose.

In one embodiment, artificial sweeteners can be used such as acesulfame K, aspartame, sucralose, d-tagatose, neotame, monatin, and acesulfame potassium (Ace-K), or combinations thereof.

In a further embodiment, sweeteners include saccharin, sodium saccharin, sodium cyclamate, acesulfame potassium, thaumatin, neohesperidin dihydrochalcone, ammonium glycyrrhizinate and aspartame.

The sweeteners involved may be selected from a wide range of materials including water-soluble sweeteners, water-soluble artificial sweeteners, water-soluble sweeteners derived from naturally occurring water-soluble sweeteners, dipeptide based sweeteners, and protein based sweeteners, including mixtures thereof. Without being limited to particular sweeteners, representative categories and examples include:

(a) water-soluble sweetening agents such as dihydrochalcones, monellin, steviosides, lo han quo, lo han quo derivatives, glycyrrhizin, dihydroflavenol, and sugar alcohols such as sorbitol, mannitol, maltitol, xylitol, erythritol, and L-aminodicarboxylic acid aminoalkenoic acid ester amides, such as those disclosed in U.S. Pat. No. 4,619,834, which disclosure is incorporated herein by reference, and mixtures thereof;

b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and mixtures thereof;

(c) dipeptide based sweeteners, such as L-aspartic acid derived sweeteners, such as L-aspartyl-L-phenylalanine methyl ester (Aspartame), N-[NI-(3,3-dimethylbutyl)-L-. alpha.-aspartyl]-L-phenylalanine 1-methyl ester (Neotame), and materials described in U.S. Pat. No. 3,492,131, L-alphaaspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(I-cyclohexen)-alanine, and mixtures thereof;

(d) water-soluble sweeteners derived from naturally occurring water-soluble sweeteners, such as chlorinated derivatives of ordinary sugar (sucrose), e.g., chiorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-l'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-I-chloro-I-deoxy-beta-D-fructo-furanoside, or 4,r-dichloro-4,r-dideoxygalactosucrose; l',6'-dichloro l',6'-dideoxysucrose; 4-chloro-4-deoxy-alpha-D-galactopyranosyl-1,6-dichloro-1,6-dideoxy-beta-D-fructofuranoside, or 4,r,6'-trichloro-4,r,6'-trideoxygalactosucrose; 4,6-dichloro-4,6-dideoxy-alpha-D-galactopyranosyl-6-chloro-6-deoxy-beta-D--fructofuranoside, or 4,6,6'-trichloro-4,6,6'-trideoxygalactosucrose; 6,r,6'-trichloro-6,r,6'-trideoxysucrose; 4,6-dichloro-4,6-dideoxy-alpha-D-galacto-pyranosyl-1,6-dichloro-1,6-dideo-xy-beta-D-fructofuranoside, or 4,6,r,6'-tetrachloro-4,6, r,6'- tetradeoxygalacto-sucrose; and 4,6, r,6'-tetradeoxy-sucrose, and mixtures thereof;

(e) protein based sweeteners such as thaumaoccous danielli (Thaumatin I and II) and talin; and (f) the sweetener monatin (2-hydroxy-2-(indol-3-ylmethyl)-4-aminoglutaric acid) and its derivatives. The intense sweetening agents may be used in many distinct physical forms well-known in the art to provide an initial burst of sweetness and/or a prolonged sensation of sweetness. Without being limited thereto, such physical forms include free forms, spray dried forms, powdered forms, beaded forms, encapsulated forms, and mixtures thereof. In one embodiment, the sweetener is a high intensity sweetener such as aspartame, sucralose, and acesulfame potassium (e.g., Ace-K or acesulfame-K).

In some embodiments, the sweetener may be a polyol. Polyols can include, but are not limited to glycerol, sorbitol, maltitol, maltitol syrup, mannitol, isomalt, erythritol, xylitol, hydrogenated starch hydrolysates, polyglycitol syrups, polyglycitol powders, lactitol, and combinations thereof.

In general, an effective amount of intense sweetener may be utilized to provide the level of sweetness desired, and this amount may vary with the sweetener selected. The intense sweetener may be present in amounts from about 0.001% to about 3%, by weight of the formulation, depending upon the sweetener or combination of sweeteners used. The exact range of amounts for each type of sweetener may be selected by those skilled in the art.

In one embodiment, the formulation may include sweeteners including, for example, sugar, glucose syrup, corn syrup, high fructose corn syrup, juice concentrate, or mixtures thereof. In one embodiment, the sweetener comprises erythritol, xylitol, sugar, glucose syrup, corn syrup, high fructose corn syrup, juice concentrate, tapioca syrup, agave syrup, brown rice syrup, high maltose syrup, invert sugar, artificial sweeteners, saccharin, saccharin salts, cyclamic acid, cyclamic acid salts, aspartame, sucralose, acesulfame, rebaudioside A, rebaudioside B, rebaudioside C, rebaudioside D, rebaudioside E, dulcoside A, dulcoside B, rubusoside, *stevia*, stevioside, mogroside IV, mogroside V, Luo Han Guo sweetener, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, cyclocarioside I, sucralose, acesulfame potassium and other salts, aspartame, alitame, saccharin, neohesperidin dihydrochalcone, cyclamate, neotame, N-[N-[3-(3-hydroxy-4-methoxyphenyl) propyl]-L-.alpha.-aspartyl]-L-phenylalanine 1-methyl ester, N-[N-[3-(3-hydroxy-4-methoxyphenyl)-3-methylbutyl]-L-alpha-aspartyl]-L-phenylalanine 1-methyl ester, N-[N-[3-(3-methoxy-4-hydroxyphenyl) propyl]-L-alpha-aspartyl]-L-phenylalanine 1-methyl ester, salts thereof, liquorice or its extracts or isolates, or a mixture thereof.

Food Acids

The pH of the formulation is about 2.5 to about 4, for example, about 2.7 to about 4, about 2.8 to about 3.7. The pH may be adjusted by a food acid, buffer, or both.

Suitable food acids include but are not limited to acetic acid, adipic acid, ascorbic acid, butyric acid, citric acid, formic acid, fumaric acid, lactic acid, phosphoric acid, malic acid, oxalic acid, succinic acid, tartaric acid, or combinations thereof.

Suitable buffers include but are not limited to: Sodium ascorbate, sodium citrate, sodium malate, sodium fumarate, potassium sodium tartrate and/or sodium tartrate.

Flavouring Agents

In some embodiments, the formulation may further include a flavouring agent. Flavouring agents may include those flavours known to the skilled artisan, such as natural and artificial flavours. These flavourings may be chosen from synthetic flavour oils and flavouring aromatics and/or oils, oleoresins and extracts derived from plants, leaves, flowers, fruits, and so forth, and combinations thereof.

In some embodiments, the flavouring agents may include mint(s), menthol, menthone, isomenthone, camphor and eucalyptol, eucalyptol, camphor, borneol, fenchone, menthone and isomenthone, isopulegol, monomenthyl succinate, and menthyl lactate, menthone, isomenthone, borneol, fenchone, *eucalyptus*, ducalyptol, ethyl benzoate, neomenthol, d-fenchone, furfurylidene butyrate, bucchu fractions, sage oil, corn mint oil, rosemary, monomenthyl succinate, amyl salicylate, eugenol, phellendrene, propyl furoate, ethyl-3-hydroxy butyrate, hexyl valerate, anisyl propionate, anysyl butyrate, dihydrocarveol, or clary sag, Non-limiting representative flavour oils include spearmint oil, cinnamon oil, oil of wintergreen (methyl salicylate), peppermint oil, Japanese mint oil, clove oil, bay oil, anise oil, *eucalyptus* oil, thyme oil, cedar leaf oil, oil of nutmeg, allspice, oil of sage, mace, oil of bitter almonds, and *cassia* oil. Also useful flavourings are artificial, natural and synthetic fruit flavours such as vanilla, and citrus oils including lemon, orange, lime, grapefruit, yazu, sudachi, and fruit essences including apple, pear, peach, grape, blueberry, strawberry, raspberry, cherry, plum, pineapple, apricot, banana, melon, apricot, ume, cherry, raspberry, blackberry, tropical fruit, mango, mangosteen, pomegranate, *papaya* and so forth. Other potential flavours whose release profiles can be managed include a milk flavour, a butter flavour, a cheese flavour, a cream flavour, and a yogurt flavour; a vanilla flavour; tea or coffee flavours, such as a green tea flavour, a oolong tea flavour, a tea flavour, a cocoa flavour, a chocolate flavour, and a coffee flavour; mint flavours, such as a peppermint flavour, a spearmint flavour, and a Japanese mint flavour; spicy flavours, such as an asafetida flavour, an ajowan flavour, an anise flavour, an *angelica* flavour, a fennel flavour, an allspice flavour, a cinnamon flavour, a camomile flavour, a mustard flavour, a cardamom flavour, a caraway flavour, a cumin flavour, a clove flavour, a pepper flavour, a coriander flavour, a *sassafras* flavour, a savoury flavour, a Zanthoxyli Fructus flavour, a *perilla* flavour, a juniper berry flavour, a ginger flavour, a star anise flavour, a horseradish flavour, a thyme flavour, a tarragon flavour, a dill flavour, a *capsicum* flavour, a nutmeg flavour, a basil flavour, a marjoram flavour, a rosemary flavour, a bay leaf flavour, and a wasabi (Japanese horseradish) flavour; alcoholic flavours, such as a wine flavour, a whisky flavour, a brandy flavour, a rum flavour, a gin flavour, and a liqueur flavour; floral flavours; and vegetable flavours, such as an onion flavour, a garlic flavour, a cabbage flavour, a carrot flavour, a celery flavour, mushroom flavour, and a tomato flavour. These flavouring agents may be used in liquid or solid form and may be used individually or in admixture. Commonly used flavours include mints such as peppermint, menthol, spearmint, artificial vanilla, cinnamon derivatives, and various fruit flavours, whether employed individually or in admixture. Flavours may also provide breath freshening properties, particularly the mint flavours when used in combination with the cooling agents, described herein below. In some embodiments, flavourants may be chosen from geraniol, linalool, nerol, nerolidal, citronellol, heliotropine, methyl cyclopentelone, ethyl vanillin, maltol, ethyl maltol, furaneol, alliaceous compounds, rose type compounds such as phenethanol, phenylacetic acid, nerol, linalyl esters, jasmine, sandlewood, patchouli, and/or cedarwood.

In some embodiments, other flavourings include aldehydes and esters such as cinnamyl acetate, cinnamaldehyde, citral diethylacetal, dihydrocarvyl acetate, eugenyl formate, p-methylamisol, and so forth may be used. Generally any flavouring or food additive such as those described in Chemicals Used in Food Processing, publication 1274, pages 63-258, by the National Academy of Sciences, may be used. This publication is incorporated herein by reference. These may include natural as well as synthetic flavours.

Further examples of aldehyde flavourings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, e.g., melonal (melon), 2,6-dimethyloctanal (green fruit), and 2-dodecenal (citrus, mandarin), cherry, grape, blueberry, blackberry, strawberry shortcake, and mixtures thereof.

In one embodiment, the flavouring agent comprises vanilla, peppermint oil, spearmint oil, *eucalyptus* oil, cinnamon oil, grapefruit oil, menthol, mono-menthyl succinate, menthol ethylene glycol carbonate, menthone glycerol ketal, menthyl lactate, (-)-isopulegol, p-menthane-3,8-diols, (-)-monomenthyl glutarate, oil of wintergreen (methylsalicy late), citrus oils, orange oils, fruit essences, Rosemary Oil, lavender oil, sage oil, clary sage oil, thyme oil, sandalwood oil, basil oil, coriander oil, cypress oil, fleabane oil, frankincense oil, geranium oil, fennel oil, oregano oil, Dalmatian sage oil, tarragon oil, or mixtures or derivatives thereof.

Colouring Agents

Colouring agents may be used in amounts effective to produce the desired colour. The colouring agents may include pigments which may be incorporated in amounts up to about 6%, by weight of the formulation. The colourants may also include natural food colours and dyes suitable for food, drug and cosmetic applications. These colourants are known as F.D.& C. dyes and lakes. The materials acceptable for the foregoing uses are preferably water-soluble. Illustrative nonlimiting examples include the indigoid dye known as F.D.& C. Blue No. 2, which is the disodium salt of 5,5-indigotindisulfonic acid. Similarly, the dye known as F.D.& C. Green No. 1 comprises a triphenylmethane dye and is the monosodium salt of 4-[4-(N-ethyl-p-sulfoniumbenzylamino) diphenylmethylene]-[I-(N-ethyl-N-p-sulfoniumbenzyl)-delta-2,5-cyclohexadieneimine], A full recitation of all F.D.& C. colourants and their corresponding chemical structures may be found in the Kirk-Othmer Encyclopaedia of Chemical Technology, 3rd Edition, in volume 5 at pages 857-884, which text is incorporated herein by reference.

In some embodiments, one or more colours can be included. As classified by the United States Food, Drug, and Cosmetic Act (21 C.F.R. 73), colours can include exempt from certification colours (sometimes referred to as natural even though they can be synthetically manufactured) and certified colours (sometimes referred to as artificial), or combinations thereof. In some embodiments, exempt from certification or natural colours can include, but are not limited to annatto extract, (El60b), bixin, norbixin, astaxanthin, dehydrated beets (beet powder), beetroot red/betanin (E162), ultramarine blue, canthaxanthin (E161g), cryptoxanthin (E161c), rubixanthin (E161d), violanxanthin (E161e), rhodoxanthin (E161f), caramel (E150 (a-d)),.beta.-apo-8'-carotenal (E160e),.beta.-carotene (E160a), alpha carotene, gamma carotene, ethyl ester of beta-apo-8 carotenal (E160f), flavoxanthin (E161a), lutein (E161b), cochineal extract (E120); carmine (E132), carmoisine/azorubine (E122), sodium copper chlorophyllin (E141), chlorophyll (E140), toasted partially defatted cooked cottonseed flour, ferrous gluconate, ferrous lactate, grape colour extract, grape skin extract (enocianina), anthocyanins (El63), haematococcus algae meal, synthetic iron oxide, iron oxides and hydroxides (E172), fruit juice, vegetable juice, dried algae meal, *tagetes* (Aztec marigold) meal and extract, carrot oil, corn endosperm oil, paprika, paprika oleoresin, phaffia yeast, riboflavin (E101), saffron, titanium dioxide, turmeric (E100), turmeric oleoresin, amaranth (E123), capsanthin/capsorbin (E160c), lycopene (E160d), and combinations thereof.

In some embodiments, certified colours can include, but are not limited to, FD&C blue #1, FD&C blue #2, FD&C green #3, FD&C red #3, FD&C red #40, FD&C yellow #5 and FD&C yellow #6, tartrazine (E102), quinoline yellow (E104), sunset yellow (El 10), ponceau (E124), erythrosine (E127), patent blue V (E131), titanium dioxide (E171), aluminium (E173), silver (E174), gold (E175), pigment rubine/lithol rubine BK (E180), calcium carbonate (E170), carbon black (E153), black PN/brilliant black BN (E151), green S/acid brilliant green BS (E142), and combinations thereof. In some embodiments, certified colours can include FD&C aluminium lakes. These include of the aluminium salts of FD&C dyes extended on an insoluble substrate of alumina hydrate. Additionally, in some embodiments, certified colours can be included as calcium salts.

In some embodiments, natural fruits or plant juice or extracts may be used as the colouring agents. Example include without limitation carrot juice, raspberry juice, blackberry juice, blueberry juice, and beet juice.

Humectant

The glycerine is a humectant and freezing point depressant. It also helps decrease the tendency for granulation and aid in maintaining softness. In some embodiments, glycerine or equivalent material may be employed at a level of from about 1 to about 5% by weight of the final product, e.g., 2 to 3%.

Humectants that can provide a perception of mouth hydration may be included. Such humectants can include, but are not limited to glycerol, sorbitol, polyethylene glycol, rythritol, and xylitol. Additionally, in some embodiments, fats can provide a perception of mouth moistening. Such fats can include medium chain triglycerides, vegetable oils, fish oils, mineral oils, and combinations thereof.

Bulking Agents

Suitable sugar bulking agents include monosaccharides, disaccharides and polysaccharides such as xylose, ribulose, glucose (dextrose), lactose, mannose, galactose, fructose (levulose), sucrose (sugar), maltose, invert sugar, partially hydrolyzed starch and corn syrup solids, and mixtures thereof.

Suitable sugar alcohol bulking agents include sorbitol, xylitol, mannitol, galactitol, lactitol, maltitol, erythritol, isomalt and mixtures thereof. Suitable hydrogenated starch hydrolysates include those disclosed in U.S. Pat. No. 4,279,931 and various hydrogenated glucose syrups and/or powders which contain sorbitol, maltitol, hydrogenated disaccharides, hydrogenated higher polysaccharides, or mixtures thereof. Hydrogenated starch hydrolysates are primarily prepared by the controlled catalytic hydrogenation of corn syrups. The resulting hydrogenate starch hydrolysates are mixtures of monomeric, dimeric, and polymeric saccharides. The ratios of these different saccharides give different hydrogenated starch hydrolysates different properties. Mixtures of hydrogenated starch hydrolysates, such as LYCASIN.RTM., a commercially available product manufactured by Roquette Freres of France, and HYSTAR.RTM., a commercially available product manufactured by SPI Polyols, Inc. of New Castle, Del., are also useful.

In one embodiment, the bulking agent comprises maltitol syrup, polydextrose, sorbitol, soluble corn fibre, resistant starch, resistant maltodextrin, cellulose, hemicellulose, fructooligosaccharides, galacto-oligosaccharides, lactulose, xylo-isomalto-oligosaccharide, soybean oligosaccharide, oligo-glucose, stachyose, lactosucrose, or a combination thereof.

Plasticizer

In some embodiments, the formulation may further include plasticizer to modify the texture of the formulation. A texture modifying agent may include a particulate material. Suitable particulate materials can include, but are not limited to, sucrose, polyols such as sorbitol, xylitol, mannitol, galactitol, lactitol, maltitol, erythritol, isomalt, hydrogenated starch hydrolysates and mixtures thereof, starches, proteins, and combinations thereof. In some embodiments, the particulate material serving as a texture modifying component is selected based on its ability or lack of ability to crystallize the saccharides in the saccharide portion. For example, when isomalt is included in the saccharide portion, sorbitol powder can be added to the formulation because it will not cause the isomalt to crystallize. Alternatively, when erythritol is included in the saccharide portion, erythritol powder can be added to the formulation because it will cause the erythritol to crystallize. Such particulates can be included in amounts from 5% to 35% w/w of the formulation.

Emulsifiers

The formulation may include an emulsifier. The emulsifier may present in an amount of from about 0.001% to about 5%, alternatively 0.001% to 1%, alternatively 1% to 3%, alternatively 3% to 5%, by weight of the formulation. In some embodiments, the emulsifier is present in an amount of from about 0% to about 5%, alternatively 0.001% to 1%, alternatively 1% to 3%, alternatively 3% to 5%, by weight of the formulation.

Example emulsifiers include but not limited to modified corn starch, mono-and diglycerides, and lecithin.

The emulsifier may assist in holding together the fats and water and other components together in a homogeneous formulation. In one embodiment, the emulsifier may assist in the formation of a "water and oil" emulsion that creates the smooth texture of the finished product.

Thickeners

The formulation may further include a thickening agent to help with the viscosity of the final product. Some thickening agents are gelling agents. Others act as mechanical thixotropic additives with discrete particles adhering or interlocking to resist strain.

In some embodiments, the thickening agent may be polysaccharides or protein. Example polysaccharides thickening agents include starches, vegetable gums and pectin. Example starch based thickening agents include arrowroot, cornstarch, katakuri starch, potato starch, sago, tapioca and their starch derivatives. Example vegetable gums based thickening agents may include alginin, guar gum, locust bean gum, and xanthan gum. Example protein based thickening agents include collagen, egg whites, furcellaran, and gelatin. Sugar based thickening agent may include agar and carrageenan Preservatives Preservatives may be natural or synthetic. Non-limiting examples of suitable preservatives include: sodium benzoate, sodium citrate, sodium phosphate, potassium metabisulfite, sodium metabisulfite, sodium lactate, sodium sulfite, EDTA (ethylenediaminetetraacetic acid), methylparaben, TBHQ, tocopherols, and mixtures thereof. Natural preservatives may include phenols (phenolic acid, polyphenols, tannins), isoflavonoids, organic acids (acetic, lactic, citric), and herb extracts such as extracts of citrus fruits, oregano, thyme, sage, rosemary, clove, coriander, garlic, and onion.

In some embodiments, the formulation may include at least about 0% to 2%, by weight of the formulation of a preservative component from above, or mixtures thereof Gelling Components The gelling component may include one or more gelling agents. A number of gelling agents may be utilized including without limitation, gelatin, pectin, gum Arabic, carrageenans, high methoxy pectin, alginates, gellan gum, modified or unmodified starches, modified starch wheat flour or enriched wheat flour or bleached flour or any type of flour from a natural source, or a combination thereof.

Other example gelling agents may include acacia, alginic acid, bentonite, Carbopols® (now known as carbomers), carboxymethyl cellulose, ethylcellulose, gelatin, hydroxyethyl cellulose, hydroxypropyl cellulose, magnesium aluminum silicate (Veegum®), methylcellulose, poloxamers (Pluronics®), polyvinyl alcohol, sodium alginate, and tragacanth.

The amount of gelling agents used in the formulation depend upon the texture, viscosity and softness of a desired product as well as other ingredients in the formulation In some embodiments, the gelling agents may be used in concentrations of about 0.5% to about 10%, about 0.1% to about 7%, or about 0.2 to about 15%.

In one embodiment, the gelatin and pectin may be employed at a weight ratio supplying at least 50% gelatin and at least 10% pectin, e.g., from about 70 to 85% gelatin and the remainder pectin.

In one embodiment, pectin may be a high methoxy pectin obtained from apples. In one embodiment, gelatin may be a type A gelatin from porcine sources. Bloom values for the gelatin may be in the range of from 100 to 280. In one embodiment, the bloom value is about 250.

In one embodiment, the combination of gelatin and pectin may be employed at a level of from about 4.5 to about 6% by weight of the final product, e.g., about 5.5% on that basis.

In one embodiment, the formulation may include gellan gum, carrageenans, or both providing a gelatin free formulation. In one embodiment, the formulation may include from about 0.25% to about 0.75% by weight gellan gum and about 2% to about 3% by weight carrageenan based on the total weight of the formulation.

In one embodiment, a combination of gellan gum at about 0.25% to about 0.75% by weight and carrageenans at about 2.5% to about 3% by weight based on total weight of the product produces a gummy formulation with TPA hardness values in excess of 20 lbs (f), and TPA cohesiveness and elasticity values of 75% to 80%.

In one embodiment, the amount of gellan gum is about 0.25 wt % to about 0.75 wt %, and about 0.25 wt % to about 0.5 wt %. In one embodiment, the amount of carrageenan is about 1.5 wt % to about 3 wt %, and about 2.5 wt % to about 3 wt %.

According to a further aspect of the invention there is provided a formulation comprising:

a) a compound of formula (I) or a salt thereof:

(I)

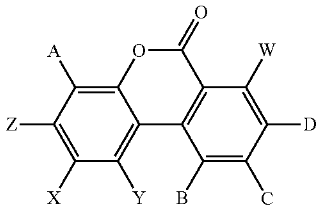

wherein:

A, B, C and D are each independently selected from H and OH;

W, X and Y are each independently selected from H and OH; and

Z is selected from H and OH; and b) pectin, for example, high methoxy pectin.

According to a further aspect of the invention, there is provided a formulation, comprising;

(a) a compound of formula (I); for example, urolithin A, and (b) pectin;

wherein the ratio of the compound of formula (I) and pectin is in the range about 1:2 (w/w) to about 10 to 1 (w/w).

According to a further aspect of the invention, there is provided a formulation, comprising;

(a) a compound of formula (I); for example, urolithin A, (b) pectin; and (c) soluble fibre, for example, soluble tapioca fibre.

According to a further aspect of the invention, there is provided a formulation, comprising;

(a) a compound of formula (I); for example, urolithin A, (b) pectin; and (c) a low calorie sweetener, for example, allulose.

According to a further aspect of the invention, there is provided a formulation, comprising;

(a) a compound of formula (I); for example, urolithin A, (b) pectin; and (c) citric acid and/or a citrate salt (for example, sodium citrate), for example, citric acid and a salt of citric acid (for example, sodium citrate).

According to a further aspect of the invention, there is provided a formulation, comprising;

(a) a compound of formula (I); for example, urolithin A, (b) pectin;

(c) soluble tapioca fibre;

(d) citric acid; and/or a citrate salt (for example, sodium citrate); and (e) a low calorie sweetener, for example, allulose.

According to a further aspect of the invention, there is provided a formulation, comprising;

(a) about 1% to about 20% (w/w), for example, about 5% to about 20% (w/w), compound of formula (I); for example, urolithin A, and (b) about 0.5% to about 4% (w/w) pectin;

According to a further aspect of the invention, there is provided a formulation, comprising;

(a) about 1% to about 20% (w/w), for example, about 5% to about 20% (w/w), a compound of formula (I); for example, urolithin A, (b) about 0.5% to about 4% (w/w) pectin; and (c) about 25% to about 45% (w/w) soluble tapioca fibre.

According to a further aspect of the invention, there is provided a formulation, comprising;

(a) about 1% to about 20% (w/w), for example, about 5% to about 20% (w/w), compound of formula (I); for example, urolithin A, (b) about 0.5% to about 4% (w/w) pectin; and (c) about 25% to about 45% (w/w) low calorie sweetener, for example, allulose.

According to a further aspect of the invention, there is provided a formulation, comprising;

(a) about 1% to about 20% (w/w), for example, about 5% to about 20% (w/w), compound of formula (I); for example, urolithin A, (b) about 0.5% to about 4% (w/w) pectin; and (c) about 1% to about 10% (w/w), for example, about 1% to 5% or about 2% to about 4%, low calorie sweetener, for example, allulose.

According to a further aspect of the invention, there is provided a formulation, comprising;

(a) about 1% to about 20% (w/w), for example, about 5% to about 20% (w/w), compound of formula (I); for example, urolithin A, (b) about 0.5% to about 4% (w/w) pectin; and (c) about 25% to about 60% (w/w), low calorie sweetener, for example, one or more low calorie sweeteners selected from allulose, fructalose, *stevia* and/or inulin.

According to a further aspect of the invention, there is provided a formulation, comprising;

(a) about 1% to about 20% (w/w), for example, about 5% to about 20% (w/w), compound of formula (I); for example, urolithin A, (b) about 0.5% to about 4% (w/w) pectin; and (c) about 0.5% to about 2% (w/w) citric acid and/or a citrate salt (for example, sodium citrate), for example, citric acid and a salt of citric acid (for example, sodium citrate).

According to a further aspect of the invention, there is provided a formulation, comprising;

(a) about 1 to about 20% (w/w), for example, about 5% to about 20% (w/w), compound of formula (I); for example, urolithin A, (b) about 0.5% to about 4% (w/w) pectin;

(c) about 25% to about 45% (w/w) soluble tapioca fibre;

(d) about 0.5% to about 2% (w/w) citric acid; and/or a citrate salt (for example, sodium citrate); and (e) about 25% to about 45% (w/w) low calorie sweetener, for example, allulose.

Embodiments of the invention comprise compound of formula (I) (for example, urolithin A) in the range about 5% to about 20% (w/w). For example, between about 5% to about 15%, for example about 5% to about 10% (w/w).

Embodiments of the invention, comprise pectin (for example, high methoxy pectin) in the range of about 0.5% to about 10% (w/w), about 0.5% to about 5% (w/w), about 0.5% to about 4% (w/w), about 0.5% to about 3% (w/w), about 0.5% to about 2% (w/w) pectin. For example, about 0.5% to about 1.5% (w/w), about 0.8% to about 1.5% (w/w), for example, about 1% to about 1.5% (w/w), for example about 1% to about 4%, or about 2% to about 4% (w/w) pectin.

Embodiments of the invention comprise soluble tapioca fibre (for example, soluble tapioca fibre syrup) in the range of about 25% to about 45% (w/w). For example, about 30% to about 40%, about 32% to about 38% (w/w).

Embodiments of the invention comprise citric acid; and/or a citrate salt (for example, sodium citrate) in the range about 0.5% to about 2% (w/w). For example, about 0.8% to about 1.5%, about 1% to about 1.5% (w/w). Salts of citric acid include sodium citrate, potassium citrate, calcium citrate and tri-ammonium citrate.

In a further aspect of the invention, formulations comprise both citric acid and a salt of citric acid. Embodiments of the invention comprise citric acid in the range of about 0.5% to about 2% (w/w). For example, about 0.5% to about 1.5%, about 0.8% to about 1.5%, about 1% to about 1,5%, about 0.8% to about 1.3% (w/w). Embodiments of the invention comprise a salt of citric acid (for example, sodium citrate) in the range of about 0.1% to about 1% (w/w). For example, about 0.1% to about 0.8%, about 0.1% to about 0.5% (w/w).

In a further aspect of the invention, formulations comprise both malic acid and sodium hydrogen malate.

Embodiments of the invention comprise low calorie sweetener, (for example, allulose) in the range about 25% to about 45% (w/w). For example, about 30% to about 40%, about 32% to about 38% (w/w).

According to a further aspect of the invention, there is provided a formulation, comprising;

(a) about 1% to about 20% (w/w), for example, about 5% to about 20% (w/w), compound of formula (I); for example, urolithin A,
(b) about 0.5% to about 4% (w/w) pectin; and
(c) about 25% to about 60% (w/w), low calorie sweetener, for example, one or more low calorie sweeteners selected from allulose, fructalose, monk fruit juice, *stevia* and/or inulin. about 10% to about 30% soluble fibre; (d)
(e) about 0.1% to about 2% sodium citrate, for example, about 0.3% to about 1% sodium citrate;
(f) optionally a pH buffer, for example, malic acid and/or sodium hydrogen malate; and
(g) optionally a colouring agent.

Compounds of Formula (I) in Amorphous Form

Compounds of Formula (I) exist in crystalline form, however, we have found that compounds of Formula (I) in amorphous form are useful in the preparation of higher bioavailability compositions. Therefore, according to a further aspect of the invention, there is provided a compound of Formula (I) in amorphous form, for example, amorphous urolithin A.

Furthermore, we have found that bioavailability can be enhanced by the addition of one or more excipients. Therefore, according to a further aspect of the invention there provided a composition comprising a compound of Formula (I), in amorphous form, for example, amorphous urolithin A and one or more excipients.

Excipients include one of more of the following: pectin, methylcellulose, hydroxypropyl methylcellulose (for example, HPMC E5), arabic gum, alginate (for example, sodium alginate, gelatin, mannitol and sorbitol. In a further embodiment excipients further include: agar, starch or modified starch.

In a further embodiment the invention provides a composition comprising a compound of Formula (I) in amorphous form and an excipient wherein the compound of Formula (I) and excipient(s) are in a ratio of 1 to about 1 to 1 to about 10, 1 to about 2 to 1 to about 10, a ratio of 1 to about 2 to 1 to about 9, a ratio of 1 to about 2 to 1 to about 8, a ratio of 1 to about 2 to 1 to about 7, a ratio of 1 to about 2 to 1 to about 6, a ratio of 1 to about 2 to 1 to about 5, for example, a ratio of 1 to about 2 to 1 to about 4, for example, a ratio of 1 to about 3, for example, wherein the excipient is selected from one or more of pectin, methylcellulose, hydroxypropyl methylcellulose (for example, HPMC E5), arabic gum, alginate and gelatin. In a further embodiment, the invention provides a composition comprising a compound of Formula (I) in amorphous form and an excipient wherein the excipient is mixture of pectin and methylcellulose.

In one embodiment, the invention comprises a compound of Formula (I) in amorphous form, for example, amorphous urolithin A, and hydroxypropyl methylcellulose (for example, HPMC E5) in a ratio of 1 to about 3.

In one embodiment, the invention comprises a compound of Formula (I) in amorphous form, for example, amorphous urolithin A, and methylcellulose in a ratio of 1 to about 3.

In one embodiment, the invention comprises a compound of Formula (I) in amorphous form, for example, amorphous urolithin A, and pectin in a ratio of 1 to about 3, ratio of 1 to about 4 or a ratio of 1 to about 5.

In one embodiment, the invention comprises a compound of Formula (I) in amorphous form, for example, amorphous urolithin A, and a mixture of excipient comprising pectin and methyl cellulose. In one embodiment the compound of Formula (I), pectin and methyl cellulose are in a ratio of 1 to about 3 to about 2.

According to a further aspect of the invention there is provided a formulation comprising:

(a) a compound of Formula (I), for example, urolithin A;
(b) pectin;
(c) a source of fibre; for example, one of more sources of fibre selected from tapioca, corn fibre and inulin;
(d) one or more sweeteners, for example, allulose and or *stevia;*
(e) water;
(f) citric acid and/or sodium citrate' (g) optionally one or more colouring agents;
(h) optionally one or more flavouring agents.

According to a further aspect of the invention there is provided a formulation comprising:

(a) a compound of Formula (I), for example, urolithin A;
(b) pectin;
(c) a source of fibre; for example, tapioca;
(d) one or more sweeteners, for example, one or more sweeteners selected from allulose, *stevia* and monk fruit juice;
(e) a pH regulator, for example, sodium hydrogen mallate;
(f) sodium citrate;
(g) water;
(h) optionally one or more colouring agents;
(i) optionally one or more flavouring agents; and
(j) optionally a coating.

Spray-dried compositions of compounds of Formula (I)

It has been found that compositions can be prepared by dissolving a compound of Formula (I), for example, urolithin A, in a solvent and spray drying. Therefore, according to a further aspect of the invention, there is provided a spray dried composition of a compound of Formula (I), for example, urolithin A.

Solvents suitable for spray drying include: ethanol and water.

In one embodiment, the solvent is water.

In a further embodiment, the solvent is ethanol.

In one embodiment, the excipient is pectin, for example, low methoxy pectin.

In a further embodiment, the excipient is a mixture of pectin and methylcellulose.

In a further embodiment, the excipient is a methylcellulose.

In a further embodiment, the excipient is is hydroxypropyl methylcellulose, for example HPMC E5.

In a further embodiment, the excipient is a gum Arabic.

In a further embodiment, the solvent is water and the excipient is pectin.

In a further embodiment, the solvent is ethanol and the excipient is pectin.

In a further embodiment of the invention, there is provided a spray dried composition of a compound of Formula (I), for example, urolithin A, comprising an excipient, for example, an excipient selected from one or more of pectin, for example, high methoxy-pectin, gum Arabic, melthylcellulose and hydroxypropyl-methylcellulose, for example, HPMC-E5, sorbitol, mannitol and sodium alginate.

In a further embodiment of the invention, there is provided a spray dried composition of a compound of Formula (I), for example, urolithin A, comprising pectin, for example, high methoxy-pectin.

In a further embodiment of the invention, there is provided a spray dried composition of a compound of Formula (I), for example, urolithin A, comprising methylcellulose.

In a further embodiment of the invention, there is provided a spray dried composition of a compound of Formula (I), for example, urolithin A, comprising gum Arabic.

In a further embodiment of the invention, there is provided a spray dried composition of a compound of Formula (I), for example, urolithin A, comprising hydroxypropyl methylcellulose, for example HPMC E5.

According to a further embodiment of the invention there is provided a process for preparing a composition comprising a compound of Formula (I), comprising:

(a) dissolving a compound of Formula (I) in a solvent to form a solution, or suspending a compound of Formula (1) in a solvent to form a suspension, for example, wherein the solvent is selected fromethanol and/or water;
(b) optionally stirring the resulting suspension or solution
(c) adding one or more excipients, for example, one or more excipients selected from pectin, methylcellulose, and hydroxypropyl methylcellulose;
(d) spray drying the solution/suspension, optionally with stirring, to form a powder; and
(e) optionally drying the powder.

According to a further embodiment of the invention, there is provided a composition preparable by a process comprising:

(a) dissolving a compound of Formula (I) in a solvent to form a solution, or suspending a compound of Formula (1) in a solvent to form a suspension, for example, wherein the solvent is selected fromethanol and/or water;
(b) optionally stirring the resulting suspension or solution
(c) adding one or more excipients, for example, one or more excipients selected from pectin, methylcellulose, and hydroxypropyl methylcellulose;
(d) spray drying the solution/suspension, optionally with stirring, to form a powder; and
(e) optionally drying the powder.

In a further embodiment of the invention, a spray dried composition comprising a compound of Formula (1) and a low methoxy pectin.

In a further embodiment a composition of the invention, comprises:

| Ingredients | Range (w/w) |
|---|---|
| Allulose | 25%-45% |
| Soluble Tapioca Fiber Syrup | 25%-45% |
| Water | 15%-25% |
| Urolithin A | 5% to 15% |
| Pectin | 2% to 10% |
| Citric Acid, | 1% to 2% |
| Stevia | 0.005%-0.010% |
| Sodium Citrate | 0.1% to 0.5% |

wherein the ranges add up to 100% with any optional colouring agents added.

In a further embodiment a composition of the invention, comprises:

| Raw material Description | Weight % (wet gummy slurry) |
|---|---|
| Allulose liquid | 1% to 5% |
| Fibersol Liquid 2 L | 10% to 30% |
| fructalose | 45% to 65% |
| Water | 1% to 3% |
| Urolithin A | 5% to 15% |
| Pectin | 1% to 4% |
| Sodium Hydrogen Malate | 0.1% to 0.4% |
| Monk Fruit Conc Juice | 0.1% to 1% |
| Stevia | 0.05% to 0.3% |
| Sodium Citrate | 0.1% to 1% |
| Malic Acid | 0.1% to 1% |

wherein the ranges add up to 100% with any optional colouring agents added.

Urolithins

Urolithins are metabolites produced by the action of mammalian, including human, gut microbiota on ellagitannins and ellagic acid. Ellagitannins and ellagic acid are compounds commonly found in foods such as pomegranates, nuts and berries. Ellagitannins are minimally absorbed in the gut themselves. Urolithins are a class of compounds with the representative structure (I) shown below. The structures of some particularly common urolithins are described in Table 1 below, with reference to structure (I).

(I)

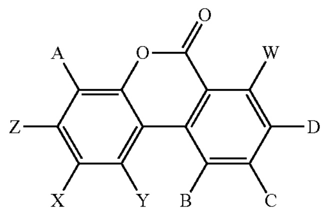

| | Substituent of structure (I) | | | | | |
|---|---|---|---|---|---|---|
| | A | B | C | D | W, X and Y | Z |
| Urolithin A | H | H | H | OH | H | OH |
| Urolithin B | H | H | H | H | H | OH |
| Urolithin C | H | H | OH | OH | H | OH |
| Urolithin D | OH | H | OH | OH | H | OH |
| Urolithin E | OH | OH | H | OH | H | OH |
| Isourolithin A | H | H | OH | H | H | OH |
| Isourolithin B | H | H | OH | H | H | H |
| Urolithin M-5 | OH | OH | OH | OH | H | OH |

-continued

| | Substituent of structure (I) | | | | | |
|---|---|---|---|---|---|---|
| | A | B | C | D | W, X and Y | Z |
| Urolithin M-6 | H | OH | OH | OH | H | OH |
| Urolithin M-7 | H | OH | H | OH | H | OH |

In practice, for commercial scale products, it is convenient to synthesise the urolithins. Routes of synthesis are described, for example, in WO 2014/004902, WO 2015/100213 and WO 2019/168972.

Urolithins of any structure according to structure (I) may be used in the combinations of the invention.

In one aspect of a combinations of the invention, a suitable compound is a compound of formula (I) wherein A, C, D and Z are independently selected from H and OH and B, W, X and Y are all H, preferably at least one of A, C, D and Z is OH.

Particularly suitable compounds are the naturally-occurring urolithins. Thus, Z is preferably OH and W, X and Y are preferably all H. When W, X and Y are all H, and A, and B are both H, and C, D and Z are all OH, then the compound is Urolithin C. When W, X and Y are all H, and A, B and C are all H, and D and Z are both OH, then the compound is urolithin A. Preferably, the urolithin used in the methods of the present disclosure is urolithin A, urolithin B, urolithin C or urolithin D. Most preferably, the urolithin used is urolithin A.

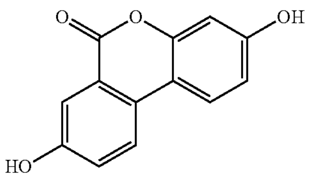

Urolithin A

According to one embodiment there is provided a combination of the invention wherein the compound of formula (I) is urolithin A.

According to one embodiment there is provided a combination of the invention wherein the compound of formula (I) is urolithin B.

According to one embodiment there is provided a combination of the invention wherein the compound of formula (I) is urolithin C.

According to one embodiment there is provided a combination of the invention wherein the compound of formula (I) is urolithin D.

In one embodiment, urolithins do not include acylated urolithins or optionally substituted acylated urolithins, (for example, acylated urolithin A, acylated urolithin B, acylated urolithin C, acylated urolithin D, acylated urolithin E, or acylated urolithin M5; orurolithin C having at least one hydroxyl substituted with a group containing a fatty acid). The term "acyl," as used herein, represents a chemical substituent of formula —C(O)—R, where R is alkyl, alkenyl, aryl, arylalkyl, cycloalkyl, heterocyclyl, heterocyclyl alkyl, heteroaryl, or heteroaryl alkyl. An optionally substituted acyl is an acyl that is optionally substituted as described herein for each group R. Examples of acyl include fatty acid acyls (e.g., short chain fatty acid acyls (e.g., acetyl)) and benzoyl.

The present invention also encompasses use of suitable salts of compounds of formula (I), e.g. pharmaceutically acceptable salts. Suitable salts according to the invention include those formed with organic or inorganic bases. Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine.

Additional Components in Formulations of the Invention:

The formulations according to the invention may contain additional components beyond the urolithin and the gelling component. The additional components may be compounds that provide health benefits, for example, a mineral formulation, an antioxidant formulation, or a mitochondria boosting formulation.

In one embodiment, the antioxidant formulation comprises bioflavonoids, resveratrol, coenzyme Q10, quercetin, rutin, lycopene, L-glutathione, N-acetyl cysteine, phenolics, anthocyanins, flavonoids, anthracenes, carotenoids, zeaxanthin, astaxanthin, xanthin, pomegranate, *Ginkgo biloba*, green tea, garlic, grapeseed, blackberry, elderberry, cranberry, blueberry, saffron, Sangre de grado (dragon's blood), lyceum barbarum (Gouqizi), its extract, powder, or isolates thereof.

In one embodiment, the mitochondria boosting formulation comprises acetyl L-carnitine, alpha-lipoic acid, coenzyme Q10 (CoQIO, or ubiquinone), nicotinamide riboside (NR), omega-3 fatty acids, magnesium, D-ribose, or a derivative or combination thereof Creatine has been described as having beneficial effects in the treatment of muscle disorders. It can be included in formulation of the invention. B-hydroxyl-B-methylbutyrate (HMB) has been described as having beneficial effects in the treatment of muscle disorders. It can be included in formulation of the invention.

In a further embodiment the formulation further comprises spermidine.

Examples of mineral formulations include potassium, chromium pocolinate, magnesium and selenium. In one embodiment, the mineral formulation may include ions of sodium, magnesium, chromium, iodine, iron, manganese, calcium, copper, fluoride, potassium, phosphorous, molybdenum, selenium, zinc, and combinations thereof. The minerals may be in the forms of salts or chelates.

Treatments:

The formulations of the invention can be taken as a single treatment or, more commonly, as a series of treatments. In one example, a subject takes a dose before or after exercise. For a subject who is not able to exercise, a dose of the formulation may, for example, be taken once, twice or three times per day, or one, two, three, four, five or six times per week. In another example, the intervention may be taken by a subject independent of the subject's ability or need to exercise. It will also be appreciated that the effective dosage of the compound may increase or decrease over the course of a particular treatment.

Medical and Non-Medical Treatments:

The formulation of the invention can be for use as a medicament. The formulation can be used as a dietary supplement, as a functional food and as a medical food. The formulation of the invention is thus useful in the treatment of various diseases as well as health conditions not considered to be a disease. In particular, disease and non-disease health conditions may be characterised by an inadequate mitochondrial activity. The formulation finds use in the treatment of both diseases and disease states. Accordingly, in an embodiment, the methods and uses of the formulations and compositions disclosed herein include non-therapeutic methods and uses. The formulation finds use in the management normal physiological function in healthy individuals of conditions characterised by poor physical performance, impaired endurance capacity, and impaired muscle function. Formulations of the invention may improve physical performance in individuals with a disease, including young and elderly individuals.

Formulations of the invention may improve physical performance, for example, short-term performance or long-term performance in healthy individuals, including athletes, non-athletic individuals, sedentary individuals and the elderly. This improvement of performance may be measured by the time spent to walk or run a certain distance (for example, an improved performance during the 6 minute walk test (MWT)), an improved time to run a certain distance, an improved IPAQ score on the international physical activity questionnaire, an increased number of chair-stands in a certain time, or another test designed to measure physical performance. In a further embodiment, the invention provides the use of a formulation of the invention for the enhancement of muscle function in people recovering from cancer.

Formulations of the invention further provide for the improvement of endurance capacity. The endurance capacity refers to the time to fatigue when exercising at a constant workload, generally at an intensity <80% $VO_2$max. Formulations of the invention may improve endurance capacity in individuals with a disease, including young and elderly individuals. Formulations of the invention may improve endurance capacity in healthy individuals, including athletes, non-athletic individuals, sedentary individuals and the elderly. The invention provides for a method of increasing the time to fatigue while performing a specific activity, for example, fitness training, walking, running, swimming, or cycling. This improvement of endurance capacity may be assessed with objective measurements (for example, speed, oxygen consumption or heart rate) or it can be self-reported measurements (for example, using a validated questionnaire).

The invention further provides a formulation to improve, maintain or reduce the loss of muscle function. Formulations of the invention may improve, maintain or reduce the loss of muscle function in individuals with a disease, including young and elderly individuals. Formulations of the invention may improve, maintain or reduce the loss of muscle function in healthy individuals, including athletes, non-athletic individuals, sedentary individuals and the elderly. For example, formulations of the invention may increase muscle strength as evidenced by the improvement of performing a physical activity, such as an exercise, for example, increased ability to lift weights or increased hand grip strength. Also, formulations of the invention may improve muscle structure, for example by increasing or maintaining muscle mass in conditions of normal muscle function, declining muscle function or impaired muscle function.

This invention further provides a formulation to improve the physical performance or endurance capacity as perceived by the individual. For example, by the reduction of in perceived exertion or effort during exercise or an activity as determined using a self-reported questionnaire.

The invention further provides a formulation of the invention for use in the treatment of a variety of conditions including conditions related to inadequate mitochondrial activity, including obesity, reduced metabolic rate, metabolic syndrome, diabetes mellitus, cardiovascular disease, hyperlipidemia, memory decline, neurodegenerative diseases, cognitive disorder, mood disorder, stress, and anxiety disorder, fatty liver disease (for example NAFLD and NASH), for improving liver function and for weight management. In particular, the formulations of the invention find use in the treatment of muscle-related pathological conditions. Accordingly, the invention provides a formulation of the invention for use in the treatment of a muscle-related pathological condition. The invention also provides a method of treating a muscle-related pathological condition in a subject comprising administering to the subject an effective amount of a formulation of the invention. Muscle-related conditions include both conditions impacting generally healthy individuals as well as pathological conditions. Such muscle conditions found in healthy people or people affected by a disease include musculoskeletal diseases or disorders; cachexia; muscle wasting; age related decline in muscle function; pre-frailty; frailty; myopathies; neuromuscular diseases, such as Duchenne muscular dystrophy and other dystrophies; age-related sarcopenia; acute sarcopenia; muscle atrophy and/or cachexia, for example muscle atrophy and/or cachexia associated with burns, bed rest, limb immobilization, or major surgery, including thoracic, abdominal, and/or orthopedic surgery; and muscle degenerative disease.

Examples of age-related conditions that may be treated with formulations of the invention include sarcopenia and muscle wasting.

The myopathy may also be caused by a muscular dystrophy syndrome, such as Duchenne.

It has been reported in WO2014/111580 that Urolithin B (but not Urolithin A) increased the mean diameter of myotubes in vitro. The effect was not seen with Urolithin A.

Non-Medical and Non-Therapeutic Treatments:

The formulation of the invention is useful in enhancing muscle performance. The invention thus provides a formulation of the invention for use in enhancing muscle performance.

The invention also provides a method of enhancing muscle performance by administering to a subject an effective amount of a formulation of the invention. Administration can be self-administration. The enhanced muscle performance may be one or more improved muscle function, improved muscle strength, improved muscle endurance and improved muscle recovery.

The formulation of the invention can thus be used in a method of improving physical endurance (e.g., ability to perform a physical task such as exercise, physical labor, sports activities), inhibiting or retarding physical fatigue, enhancing working capacity and endurance, reducing muscle fatigue, enhancing cardiac and cardiovascular function.

Improved muscle function can be particularly beneficial in elderly subjects with reduced muscle function as a result of an age-related condition. For example, a subject who may benefit from improved muscle function may experience a decline in muscle function which then leads to pre-frailty and frailty. Such subjects may not necessarily experience muscle wastage in addition to their decline in muscle function. Some subjects do experience both muscle wasting and a decline in muscle function, for example subjects with sarcopenia. The formulation of the invention may be used in enhancing muscle performance by administering a formulation of the invention to a subject who is frail or pre-frail.

Muscle performance may be sports performance, which is to say the ability of an athlete's muscles to perform when participating in sports activities. Enhanced sports performance, strength, speed, and endurance are measured by an increase in muscular contraction strength, increase in amplitude of muscle contraction, or shortening of muscle reaction time between stimulation and contraction. Athlete refers to an individual who participates in sports at any level and who seeks to achieve an improved level of strength, speed, or endurance in their performance, such as, for example, body builders, bicyclists, long distance runners, and short distance runners. Enhanced sports performance is manifested by the ability to overcome muscle fatigue, ability to maintain activity for longer periods of time, and have a more effective workout.

Urolithin Administration/Dosage Regimes

The combinations of the present disclosure involve oral administration of a urolithin of formula (I) or salt thereof to a subject in a daily amount in the range of 1.7 to 6.0 mmol per day, for example, from 1.7 to 2.7 mmol per day, or from 2.8 to 6.0 mmol per day, for a period between 2 to 16 weeks prior to vaccination. As discussed below, administration of is preferred in the range 250 mg to 1000 mg urolithin A (which corresponds to about 1.1 to 4.4 mmol) results in a surprisingly good pharmacokinetic profile, compared with a much higher dosage of 2000 mg. In one embodiment the dose is 250 mg/day, in an alternative embodiment the dose is 500 mg/day and in another embodiment the dose is 1000 mg/day.

In a further embodiment, administration doses are selected from:

–250 mg once or twice a day;
–500 mg once or twice a day;
–750 mg once or twice a day;
–1000 mg once or twice a day;
–1250 mg once or twice a day; or
–1500 mg once or twice a day.

The methods of the present disclosure involve daily administration of the compound of formula (I) or salt thereof, or of a formulation containing the compound or salt. In some embodiments the compound or formulation is administered once per day, i.e. the compound or formulation is to be administered at least once per 24 hour period. In other embodiments the compound, or formulation comprising the compound, is administered multiple times per day, for example twice per day, or three or four times per day. In such cases, the daily dosage is divided between those multiple doses. In one embodiment administration is once a day, in a second embodiment administration is twice a day, in a third embodiment administration is three times a day.

The methods of the present disclosure would usually require daily administration of the compound of formula (I) or salt thereof, or of a formulation containing the compound or salt, for a period over several months. In some embodiments, the methods may involve administration of the compound of formula (I), or salt thereof, over for example daily for at least 2 weeks, 3 weeks, 4 weeks, 5 weeks, 6 weeks, 8 weeks, 12 weeks, 4 months, 6 months, or for at least a year. In some embodiments, the method comprises administering the compound or salt thereof daily for a period of up to 3 months, up to 6 months, up to 1 year, up to 2 years or up to 5 years. In some embodiments, the method comprises administering the compound or salt daily for a period in the range of from 21 days to 5 years, from 21 days to 2 years, from 21 days to 1 year, from 21 days to 6 months, from 21 days to 12 weeks, from 28 days to 5 years, from 28 days to 2 years, from 28 days to 1 year, from 28 days to 6 months, from 28 days to 4 months, from 28 days to 12 weeks, 6 weeks to 2 years, from 6 weeks to 1 year, from 8 weeks to 1 year, or from 8 weeks to 6 months.

The methods of the present disclosure require daily administration of an amount of compound of formula (I) or salt thereof, of from 0.7 mmol per day up to 2.7 mmol per day thereof or from 0.7 mmol twice per day up to 2.7 mmol twice a day. In some embodiments, the amount administered is in the range of from 2.0 to 2.5 mmol. In some embodiments, the amount administered is approximately, 1.1, 1.2, 1.3, 1.4. 1.5, 1.6 1.7, 1.8, 1.9, 2.0, 2.1, 2.2, 2.3, 2.4, 2.5, 2.6, or 2.7 mmol per day. In other embodiments, the amount administered is approximately, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mmol per day. In some preferred embodiments the method involves administration of approximately 2.2 mmol per day or 2.2 mmol twice per day of the compound of formula (I) or salt thereof (e.g. of urolithin A). The exact weight of compound that is administered depends on the molecular weight of the compound that is used. For example, urolithin A has a molecular weight of 228 g/mol (such that 2.20 mmol is 501.6 mg) and urolithin B has a molecular weight of 212 g/mol (such that 2.20 mmol is 466.4 mg).

In a further embodiment, the methods of the present disclosure require daily administration of an amount of compound of formula (I) or salt thereof, of from 2.8 mmol per day up to 6.0 mmol per day or twice per day thereof. In some embodiments, the amount administered is in the range of from 4.0 to 4.8 mmol. In some embodiments, the amount administered is approximately, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mmol. In some preferred embodiments the method involves administration of approximately 4.4 mmol per day or twice per day of the compound of formula (I) or salt thereof (e.g. of urolithin A). The exact weight of compound that is administered depends on the molecular weight of the compound that is used. For example, urolithin A has a molecular weight of 228 g/mol (such that 4.40 mmol is 1003.2 mg) and urolithin B has a molecular weight of 212 g/mol (such that 4.40 mmol is 932.8 mg).

In some embodiments the methods involve administration of urolithin A in an amount in the range of from 400 to 600 mg/day or 400 to 600 mg once per day. In a preferred embodiment the method involves administration of urolithin A in an amount in the range of from 450 to 550 mg, more preferably approximately 500 mg per day.

In other embodiments the methods involve administration of urolithin A in an amount in the range of from 700 to 1300 mg/day per day, or in the range of from 750 to 1250 mg, or in the range of from 800 to 1200 mg, or in the range of from 850 to 1150 mg, or in the range of from 900 to 1100 mg per day. In a preferred embodiment the method involves administration of urolithin A in an amount in the range of from 950 to 1150 mg/day, more preferably approximately 1000 mg/day.

In some preferred embodiments, the methods involve administering urolithin A to the subject in an amount in the range of from 4.5 to 11 mg/kg/day, such as 4.5 to 8.5 mg/kg/day. In another embodiment, the methods involve administering urolithin A to the subject in an amount in the range of 5 to 9 mg/kg/day. In another embodiment, the methods involve administering urolithin A to the subject in an amount in the range of from 6.0 to 8 mg/kg/day.

In other preferred embodiments, the methods involve administering urolithin A to the subject in an amount in the range of from 9 to 18 mg/kg/day such as 9 to 17 mg/kg/day. In another embodiment, the methods involve administering urolithin A to the subject in an amount in the range of from 10 to 17 mg/kg/day. In another embodiment, the methods involve administering urolithin A to the subject in an amount in the range of from 11 to 16 mg/kg/day.

Dosage regimes which combine a 500 mg dose and a 1000 mg dose may be advantageous. For example, a twice daily dosage regime which combines a first dose of 1000 mg and a second dose several hours later of 500 mg. Said 500 mg dose may be 6-18 hours after the 1000 mg dose, for example 8-12 hours after the 1000 mg dose. For example, about 12 hours after the 1000 mg dose. Thus, according to a further aspect of the invention there is provided the treatment of a disease with a compound of Formula (I) which comprises a twice daily dosage regime comprising a first dose of 1000 mg, followed by a second dose of 500 mg wherein the two doses are separated by 6-18 hours.

The compound of formula (I) or salt thereof, or formulation containing the compound of salt, may be administered at any suitable time, for example it may be administered in the morning after sleep or in the evening. In some embodiments it may be preferable for the method to be performed at approximately the same time(s) each day, for example within 15, 30, 60 or 120 minutes of a given time point.

The appropriate dose of a formulation of the invention is chosen based on clinical indications by a treating physician or the non-therapeutic treatment.

In some preferred embodiments, formulations of the invention comprises a compound of formula (I) or salt thereof (e.g. urolithin A), with a preferred particle size distribution. A particular particle size distribution enables the compound of formula (I) to disperse or dissolve more rapidly. A particular particle size distribution can be achieved by methods established in the art, for example compressive force milling, hamermilling, universal or pin milling, or jet milling (for example spiral jet milling or fluidised-bed jet milling) may be used. Jet milling is especially suitable. Furthermore, a particular particle size distribution may also be directly derived by the use of a particular chemical process. If a particular particle size distribution distribution is used, then preferably the compound has a $D_{50}$ size of under 100 μm—that is to say that 50% of the compound by mass has a particle diameter size of under 100 μm. More preferably, the compound has a $D_{50}$ size of under 75 μm, for example under 50 μm, for example under 25 μm, for example under 20 μm, for example under 10 μm. More preferably, the compound has a $D_{50}$ in the range 0.5-50 μm, for example 0.5 to 20 μm, for example 0.5 to 10 μm, for example 1.0 to 10 μm, for example 1.5 to 7.5 μm, for example 2.8 to 5.5 μm. Preferably, the compound has a $D_{90}$ size of under 100 μm. More preferably, the compound has a $D_{90}$ size of under 75 μm, for example under 50 μm, for example under 25 μm, for example under 20 μm, for example under 15 μm. The compound preferably has a $D_{90}$ in the range 5 to 100 μm, for example 5 to 50 μm, for example 5 to 20 μm, for example 7.5 to 15 μm, for example 8.2 to 16.0 μm. Preferably, the compound has a $D_{10}$ in the range 0.5-1.0 μm. Preferably, the compound of formula (I) or salt thereof (e.g. urolithin A) has a $D_{90}$ in the range 8.2 to 16.0 μm, a $D_{50}$ in the range 2.8 to 5.5 μm and a $D_{10}$ in the range 0.5 to 1.0 μm.

In a further embodiment, the compound of formula (I) or salt thereof has a particle size distribution selected from one of the following:

(i) $D_{50}$ size in the range 0.5 to 50 μm and a $D_{90}$ size in the range 5 to 100 μm, (ii) the compound has a $D_{90}$ size in the range 8.2 to 16.0 μm, a $D_{50}$ size in the range 2.8 to 5.5 μm and a $D_{10}$ size in the range 0.5 to 1.0 μm;

(iii) the compound of Formula (I) has a $D_{50}$ size in the range 0.5 to 20 μm and a $D_{90}$ size in the range 5 to 50 μm;

(iv) the compound of Formula (I) has a $D_{50}$ size under 50 μm and a $D_{90}$ size under 75 μm;

(v) the compound of Formula (I) has a $D_{50}$ size under 25 μm and a $D_{90}$ size under 50 μm;

(iv) the compound of Formula (I) has a $D_{50}$ size under 10 μm and a $D_{90}$ size under 20 μm;

(v) the compound of Formula (I) has a $D_{50}$ size under 10 μm and a $D_{90}$ size under 15 μm; or (vi) the compound of Formula (I) has a $D_{50}$ size of 10 μm and a $D_{90}$ size of 20 μm.

Pharmaceutical formulations containing the compound of formula (I) or salt thereof may for example include additional pharmaceutically active compounds.

A unit dose formulation used in the methods described herein preferably contains 250 mg or 500 mg of the compound of formula (I), for example 250 mg or 500 mg of urolithin A.

The term 'artificial sweetener' refers to any sweetener, which does not occur in nature The term "carrier" refers to a diluent, adjuvant, excipient, or vehicle with which the therapeutic is administered.

The term 'fibre' refers to plant derived carbohydrates which the human digestive system is incapable of breaking down.

The term 'esterification range' (DE-degree of esterification) when related to pectin refers to the percentage of esterified carboxyl groups to total carboxyl groups in pectin. Pectin is divided into low-ester pectin (DE<50%) and high-ester pectin (DE>50%)

The term 'excipient' refers to a substance formulated alongside the active ingredient of a medication, included, for example, for the purpose of long-term stabilization, bulking up solid formulations that contain potent active ingredients in small amounts (thus often referred to as "bulking agents", "fillers", or "diluents"), or to confer a therapeutic enhancement on the active ingredient in the final dosage form, such as facilitating drug absorption, reducing viscosity or enhancing solubility.

The term 'gelling component' refers to one or more components which serves to form the polymeric matrix providing the chewable texture to the formulation.

The terms "gummy" refers to a dosage form which retains its integrity and texture upon chewing, does not initially break into discrete, solid particulates upon chewing, utilizes a gelling matrix, and is intended to be swallowed. The term 'chewable formulation' refers to a gummy. The term gummy is distinct from a jelly which is a much softer gelatinous matrix, made with, for example, agar.

The term 'healthspan' refers to the number of years that someone lives or can expect to live in reasonably good health.

The term 'pectin' refers to a mixture of complex polysaccharides that are present in the primary cell walls of a plant, and are abundant in the green parts of terrestrial plants. Pectin may be high methoxy pectin or low methoxy pectin. The term pectin further comprises amidated pectin, for example, amidated low methoxy pectin.

The term "pharmaceutically acceptable" means approved by a regulatory agency of the Federal or a state government or listed in the U.S. Pharmacopeia or other generally recognized pharmacopeia for use in animals, and more particularly in humans.

The term, "separate" administration means the administration of each of two or more compounds to a patient from non-fixed dose dosage forms simultaneously, substantially concurrently, or sequentially in any order. There may, or may not, be a specified time interval for administration of each the compounds.

The term "sequential" administration means the administration of each of two or more compounds to a patient from non-fixed (separate) dosage forms in separate actions. The administration actions may, or may not, be linked by a specified time interval. For example, administering compounds over a specified time such as once every 14 to 21 days . . .

The term "simultaneous" administration means the administration of each of two or more compounds to a patient in a single action such as where each compound are administered independently at substantially the same time or separately within time intervals that allow the compounds to show' a cooperative therapeutic effect.

The term 'sweetener system' refers to a sweetener or combination of sweeteners.

EXAMPLES

The invention will now be illustrated with respect to the following non-limiting examples

Example 1: Pectin Formulation

An example formulation of the invention consists of

| Ingredients | % by total ingredient mass |
|---|---|
| Allulose Crystalline Powder, organic | 33.54% |
| Water (soft, filtered, municipal) | 19.98% |
| Apple Juice Concentrate, 70 Brix | 19.38% |
| Urolithin A | 9.17% |
| Elderberry Juice Concentrate, 65 Brix, organic | 3.73% |
| Soluble Tapioca Fibre powder, organic | 3.73% |
| Apple Puree, 38 Brix | 3.50% |
| Ascorbic Acid, Fine Granular | 2.42% |
| Pectin, Slow-Set High-Methoxyl | 1.64% |
| Sodium Ascorbate | 1.36% |
| Clarified Lemon Juice Concentrate, 44 Brix | 0.86% |
| Zinc Citrate, Dihydrate Purified | 0.29% |
| Selenium Methionine | 0.09% |
| Vitamin D3 100 CWD EU | 0.07% |
| Flavours | Minimum 0.23% |

Example 2: Process for the Preparation of the Formulation of Example 1

1) Blend fruit concentrates, purees, water, and sodium ascorbate together in a container larger enough to hold them.

2) Blend pectin and 10 times its weight of allulose together in a container large enough to hold them.

3) Blend the following dry ingredients together in a container large enough to hold them (i.e., the remainder of allulose, the urolithin A, all vitamins (except the ascorbic acid), all minerals, and the tapioca fibre)

4) Measure out lemon concentrate and add the natural flavour to it.

5) Measure out the ascorbic acid.

6) Measure out the colour and blend it into just enough water to create a thick liquid.

7) Add the ingredients from #1 above into the confectionery kettle at room temperature.

8) Gradually whisk the ingredients from #2 above into the ingredients in the kettle. Allow to hydrate for 5-10 minutes and whisk well once more.

9) Gradually whisk the ingredients from #3 above into the ingredients in the kettle.

10) While monitoring the temperature of the gummy solution, heat relatively rapidly while stirring the mixture, avoiding extreme temperatures that could cause scorching.

11) When the solution begins to boil, pay close attention to the temperature, which should eventually rise to 230 F.

12) Immediately remove the gummy solution from the heat at this time.

13) Once cooled to approximately 220 F, stir in the following ingredients until homogenous: lemon concentrate with the natural flavour and the ascorbic acid.

14) Finally, add the liquid colour and stir until homogenous.

15) Transfer the well mixed gummy solution to a heated holding tank with agitator in preparation for depositing into molds. Temperature should be maintained such that the high-methoxyl pectin does not begin to gel prior to molding.

16) Cool the deposited gummy solution in the molds until gelation has occurred and they are firm enough to be demolded and a carnauba wax or other coating applied via panner or other means to keep the gummies from sticking.

Example 3: Pectin Formulation

An example formulation of the invention comprises:

| Ingredients | g per dose |
|---|---|
| Allulose Crystalline Powder, organic | 1.84 g |
| Urolithin A | 500 mg |
| Soluble Tapioca Fibre powder, organic | 0.21 g |
| Pectin, Slow-Set High-Methoxyl | 0.14 g |
| Zinc bisglycinate chelate | 6 mg |
| Selenium Methionine | 30 µg |
| Vitamin C | 226 mg |
| Vitamin D3 100 CWD EU | 11 µg |
| Flavours | Minimum 0.23% |

The formulation further comprises water, Apple Juice Concentrate, Clarified Lemon Juice Concentrate, Elderberry Juice Concentrate and Apple Puree and flavourings (minimum 0.23% (w/w).

Example 4-Preparation of Spray Dried Urolithin a compositionsResults

Figure 3:
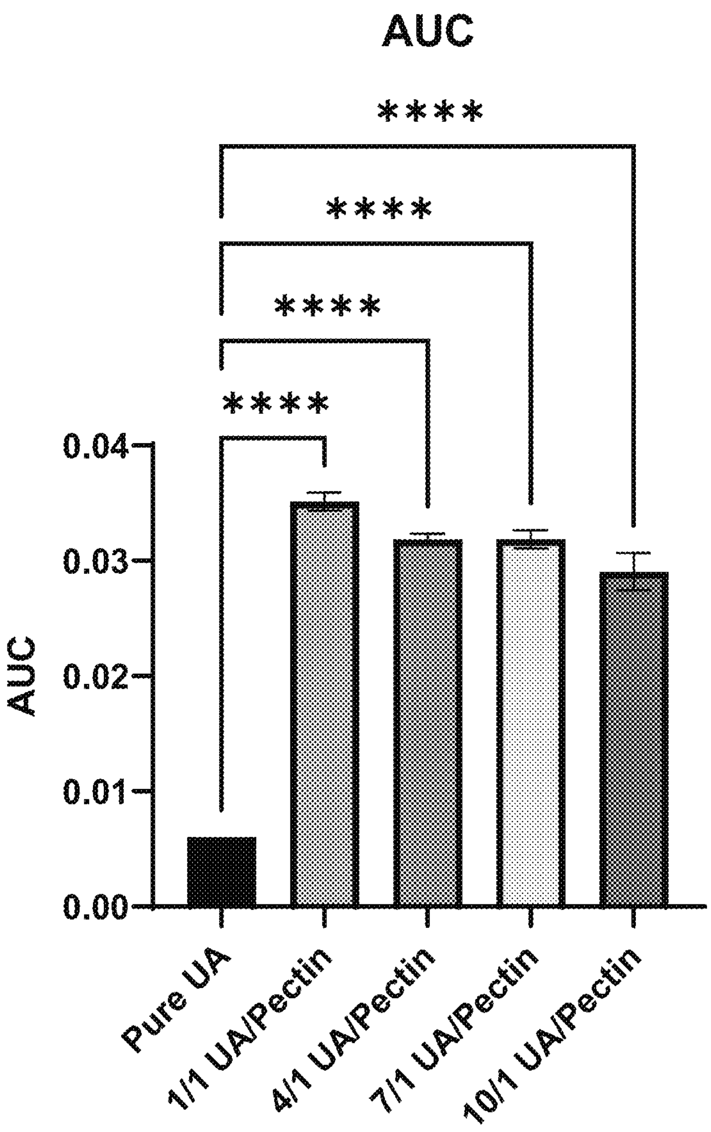
FIG. 3: AUC of powders containing the equivalent of 10 mg UA complexed with Citrus pectin in FaSSIF medium compared to 10 mg of pure UA powder, using water as solvent. Data expressed as mean +/−SD. Adjusted P Value ****<0.0001, One-way ANOVA.
Figure 4:
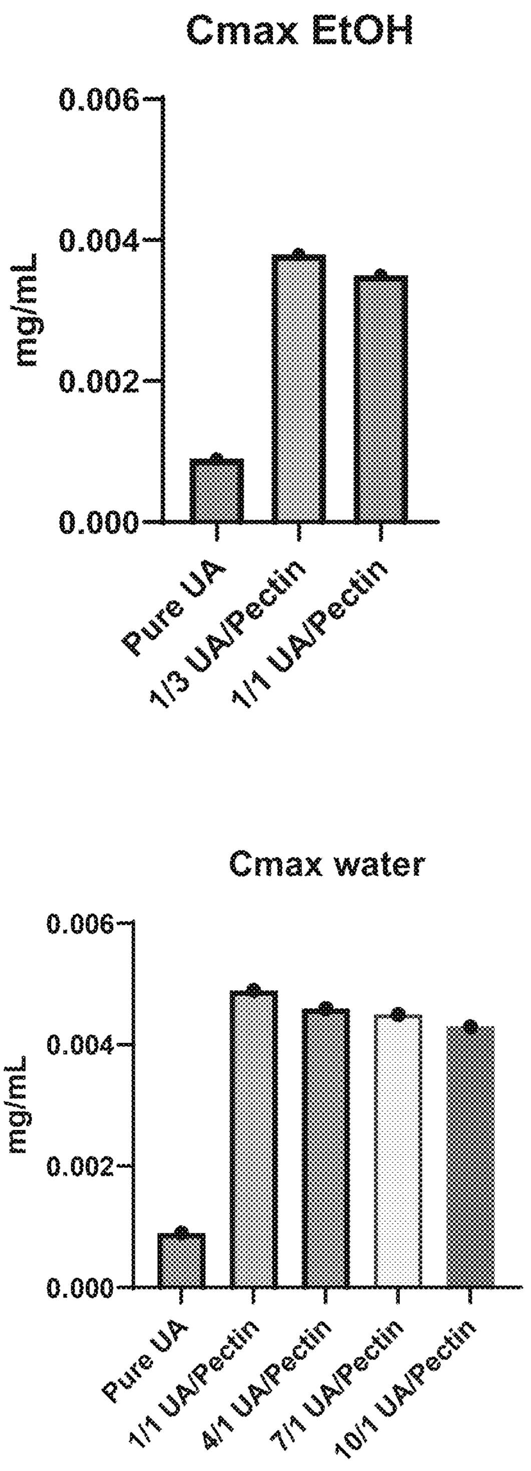
FIG. 4: Comparison of the solubility of the different Urolithin A formulations-maximum concentration of urolithin A in solution achieved comparing formulations with UA prepared in Ethanol or in water (Cmax).

Ethanol was used as solvent to prepare a stable UA suspension and a stable Citrus pectin (lot number SLBV5461, Sigma Life Science) suspension. Both suspensions were stirred minimal for 1 hour. Suspension were mixed to obtain suspension in which UA and Citrus pectin were at a w/w ratio of either UA/pectin 1/3 or 1/1. Following spray drying, the two resulting UA/Pectin powder formulations were analyzed for their solubility when dissolved in a biorelevant medium recapitulating a gut-like environment (FaSSIF, ph=6.5). Solubility of the UA/Pectin formulations were compared to solubility of pure UA powder. For both pure UA powder and UA/pectin formulations, an equivalent dose of 10 mg UA was added to FaSSIF medium. Solubility was analysed by UPLC method (Ultra-Performance Liquid Chromatography) at different time points after addition of powders to the FaSSIF medium. UA/Pectin powders showed a strikingly enhanced solubility profile at both ratios tested, when compared to pure UA powder (FIG. 3).

We further tested UA/Pectin based formulation using water as solvent, instead of ethanol. UA was dissolved in water to form a stable suspension. Citrus pectin (lot number SLBV5461, Sigma Life Science) was dissolved in water to form a solution. The UA suspension in water was complexed with Citrus pectin solution (lot number SLBV5461, Sigma Life Science) at different ratios. One ratio w/w was UA/Pectin 1/1 that showed positive data in the formulation using EtOH as solvent. We also tested a formulation with lower Pectin content, in particular formulations with UA/pectin ratio: 4/1 w/w, 7/1 w/w, 10/1 w/w.

Figure 2:
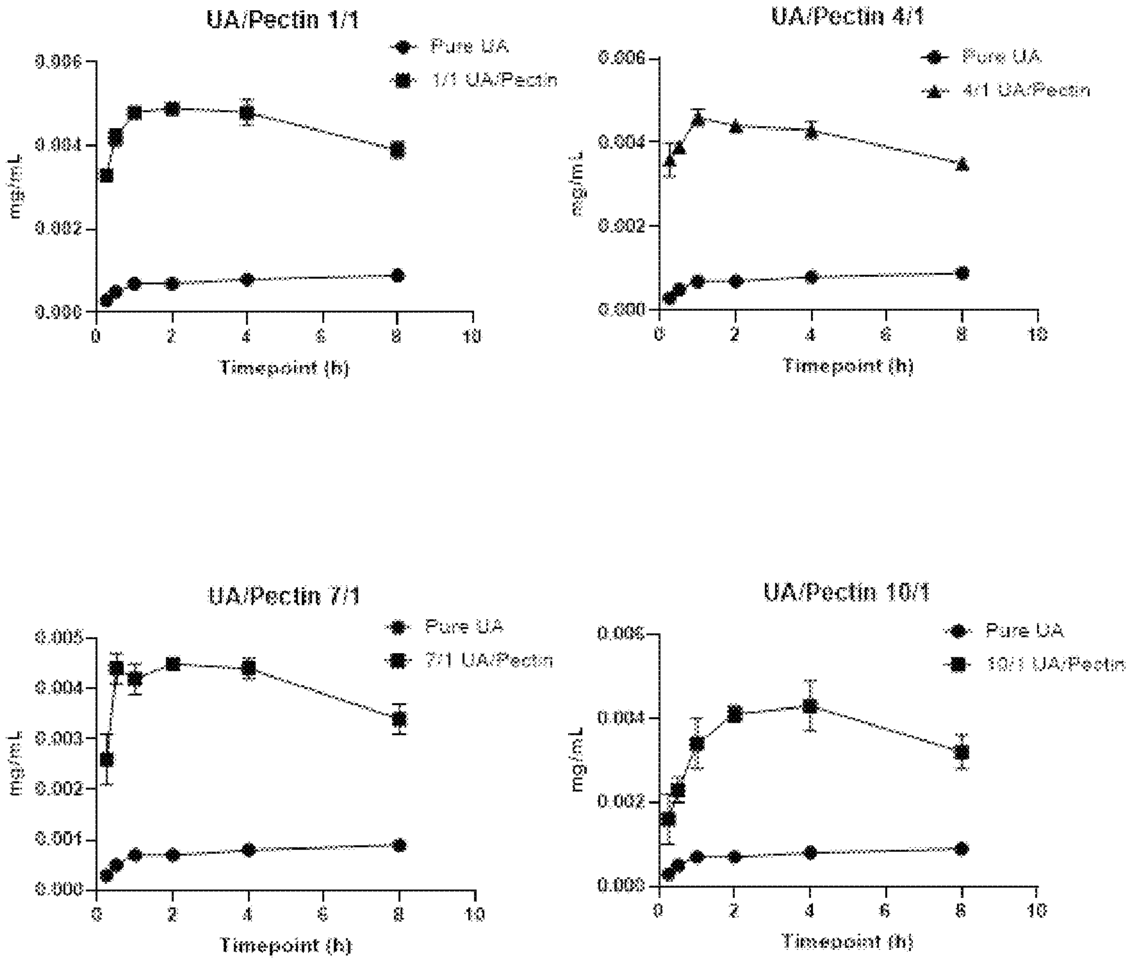
FIG. 2: Dissolution profiles of powders containing the equivalent of 10 mg UA complexed with Citrus pectin in FaSSIF medium compared to 10 mg of pure UA powder, using water as solvent. Top left graph: comparison of a formulation UA/Pectin in which excipients are in a w/w ratio of 1/1. Top right graph: comparison of a formulation UA/Pectin in which excipients are in a w/w ratio of 4/1. Bottom left graph: comparison of a formulation UA/Pectin in which excipients are in a w/w ratio of 7/1. Bottom right graph: comparison of a formulation UA/Pectin in which excipients are in a w/w ratio of 10/1.
Figure 5:
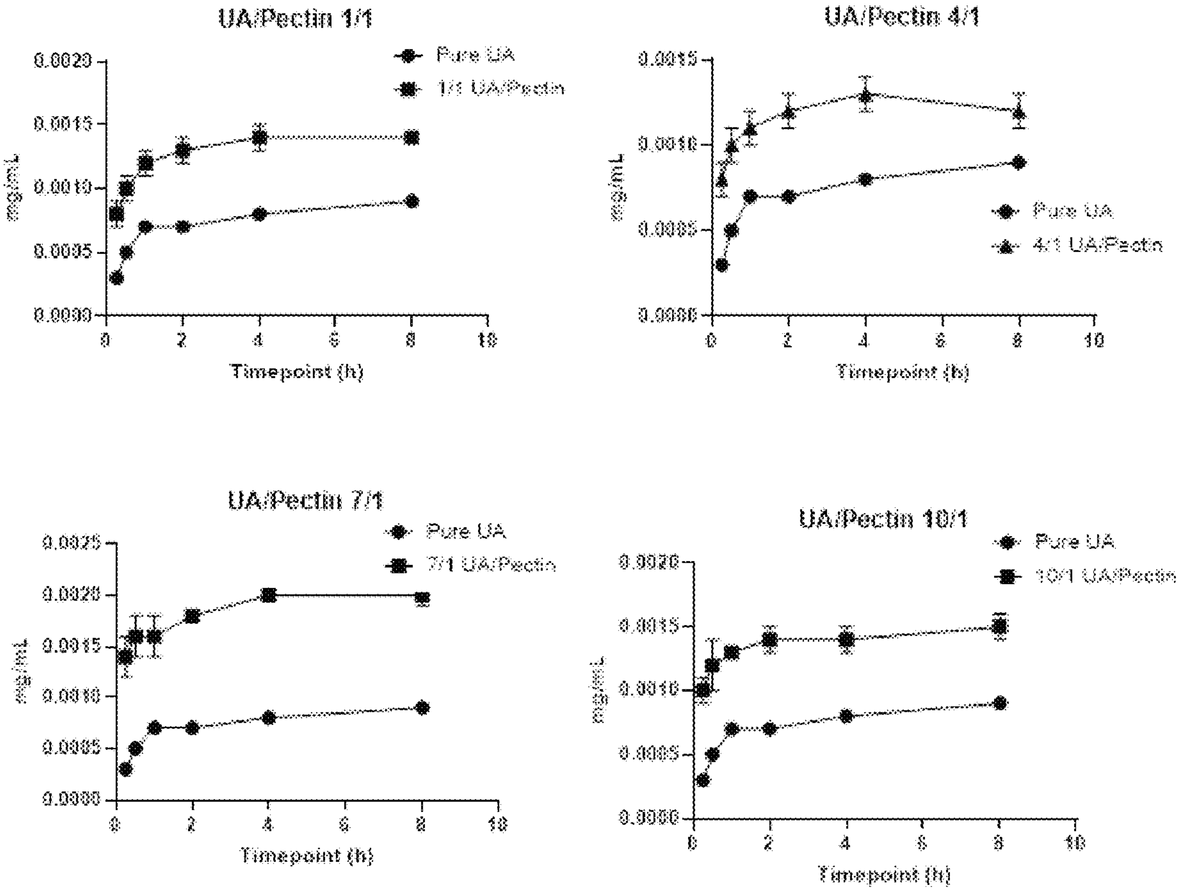
FIG. 5: Dissolution profiles of powders containing the equivalent of 10 mg UA after physical mixture (without spray drying) with Citrus pectin in FaSSIF medium compared to 10 mg of pure UA powder, using water as solvent. Top left graph: comparison of a formulation UA/Pectin in which excipients are in a w/w ratio of 1/1. Top right graph: comparison of a formulation UA/Pectin in which excipients are in a w/w ratio of 4/1. Bottom left graph: comparison of a formulation UA/Pectin in which excipients are in a w/w ratio of 7/1. Bottom right graph: comparison of a formulation UA/Pectin in which excipients are in a w/w ratio of 10/1.

Powders containing the equivalent of 10 mg UA complexed with pectin at different ratio and 10 mg of pure UA powder were analyzed for their solubility profile when dissolved in a biorelevant medium recapitulating a gut-like environment (FaSSIF, ph=6.5). Solubility was analysed by UPLC method Ultra-Performance Liquid Chromatography at different time points after addition of powders to the FaSSIF medium. UA/Pectin powders showed a strikingly enhanced solubility profile at all ratios tested (FIG. 2). This was confirmed by calculating the area under the curve (AUC) of the dissolution profiles, in order to quantify the total presence of soluble UA over time. All UA/Pectin powders showed a significant increase in AUC (FIG. 5). Surprisingly the increase in AUC was not proportional, with ratio 1:1 showing the highst AUC, the 1:4 and 1:7 ratios showing similar profiles and solubility enhancement starting to decrease only when lowering the pectin ratio to UA/Pectin 10/1 (FIG. 5).

To compare the ability to increase UA solubility of the different formulations, we also calculated the maximum concentration of UA in solution achieved comparing formulations with UA prepared in Ethanol or in water (Cmax).

For the formulations using ethanol as solvent, Cmax was 0.0009 for the pure UA powder, 0.0038 for the UA/Pectin 1/3 powder and 0.0035 for the UA/Pectin 1/1 powder. This indicates that complexing UA with pectin-using ethanol as solvent-allows an increase in solubility Cmax by 322% with the ratio UA/pectin 1/3 and by 288% with the ratio UA/pectin 1/1 (FIG. 5).

Figure 6:
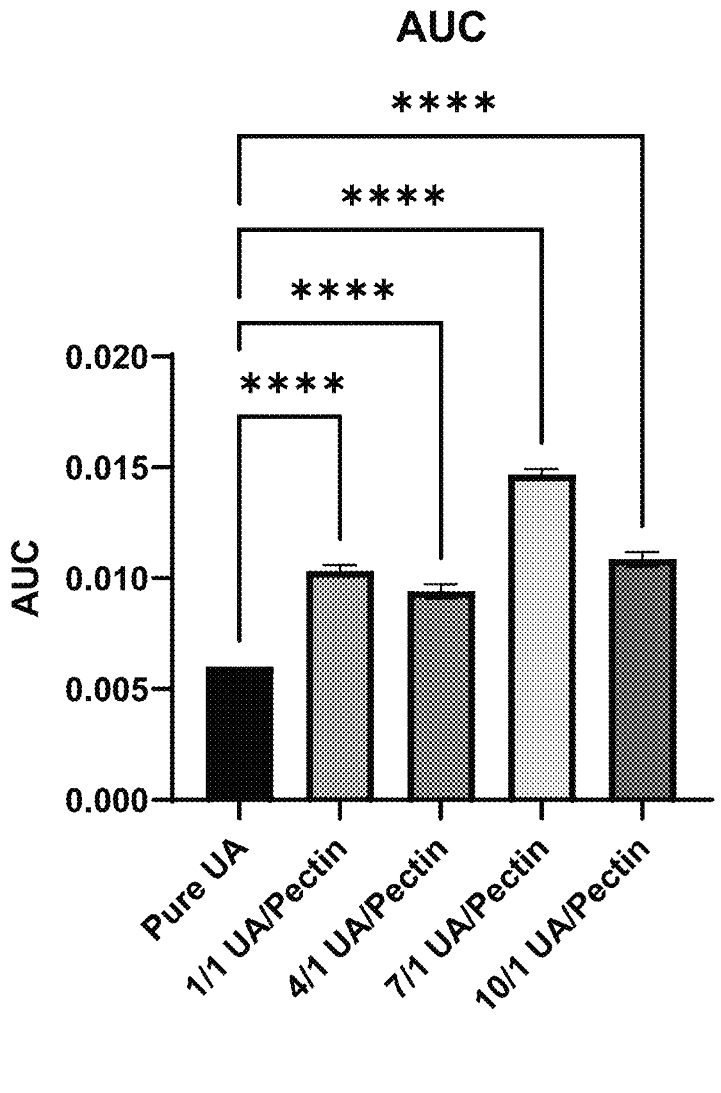
FIG. 6: AUC of powders containing the equivalent of 10 mg UA added as physical mixture, without spray drying, with Citrus pectin in FaSSIF medium compared to 10 mg of pure UA powder, using water as solvent. Data expressed as mean+/−SD. Adjusted P Value ****<0.0001, One-way ANOVA.

For the formulations using water as solvent, Cmax was 0.0009 for the pure UA powder, 0.0049 for the UA/Pectin 1/1 powder, 0.0046 for the UA/Pectin 4/1 powder, 0.0045 for the UA/Pectin 7/1 powder, 0.0043 for the UA/Pectin 10/1 powder. This indicates that complexing UA with pectin-using ethanol as solvent-allows an increase in solubility Cmax by 444% with the ratio UA/pectin 1/1, by 411% with the ratio UA/pectin 4/1, by 400% with the ratio UA/pectin 7/1, by 377.78% with the ratio UA/pectin 10/1 (FIG. 6).

This data indicates that using water as solvent leads to formulations with better UA solubility compared to using ethanol as solvent, after spray drying.

Formulations tested above have been generated by spray drying solutions/suspensions of UA and Pectin. The rationale was to improve the solubility of UA by reducing its crystalline state in favour of an amorphous state.

Figure 7:
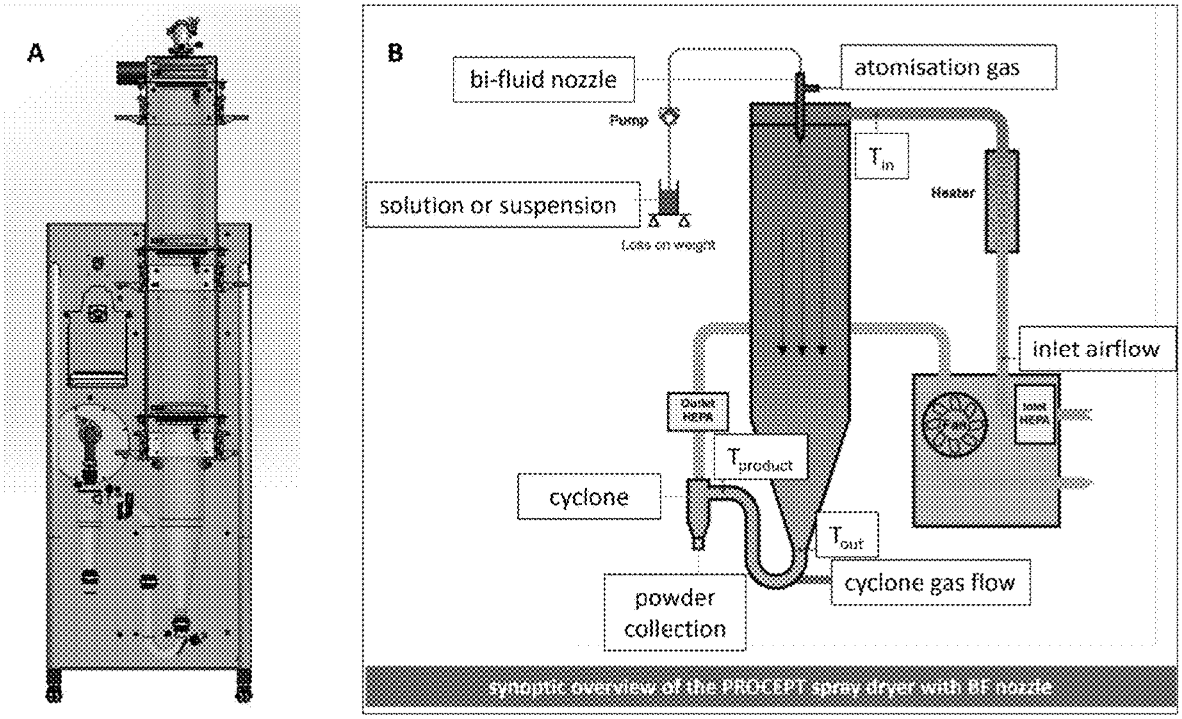
FIG. 7: A synoptic overview of the PROCEPT spray dryer with BF nozzle.

We also determined the solubility of UA following simple physical mixture of UA and Pectin, without spray drying. Surprisingly, all formulations tested showed increased UA solubility despite spray drying not being used (FIG. 7).

Figure 8:
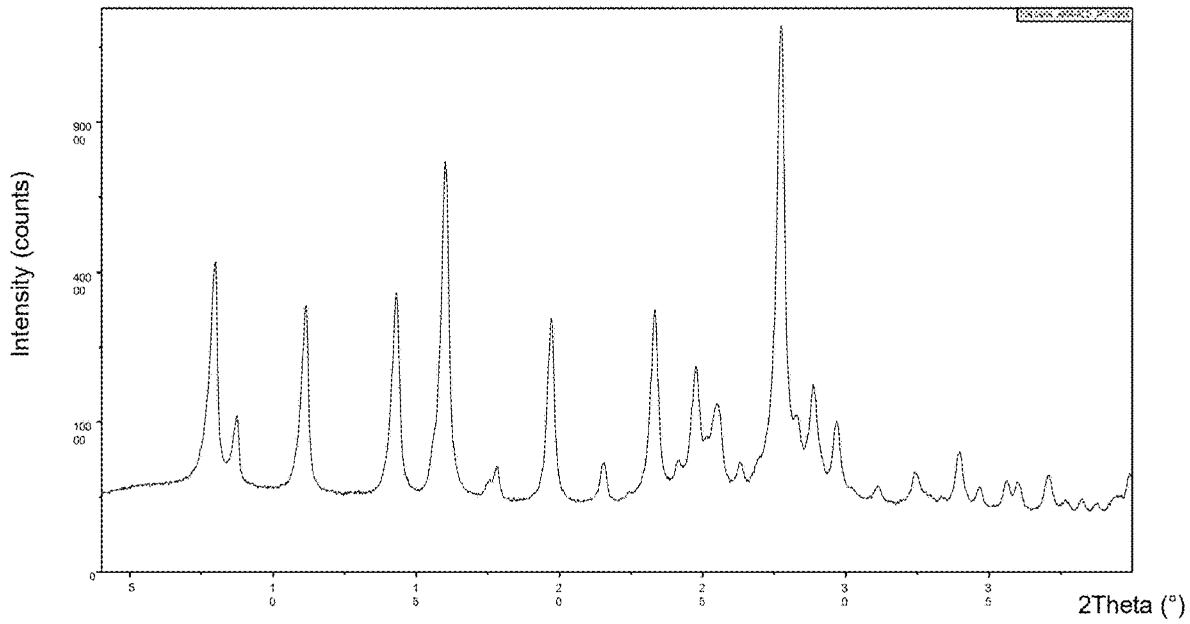
FIG. 8: shows an XRPD spectrum of crystalline urolithin A
Figure 9:
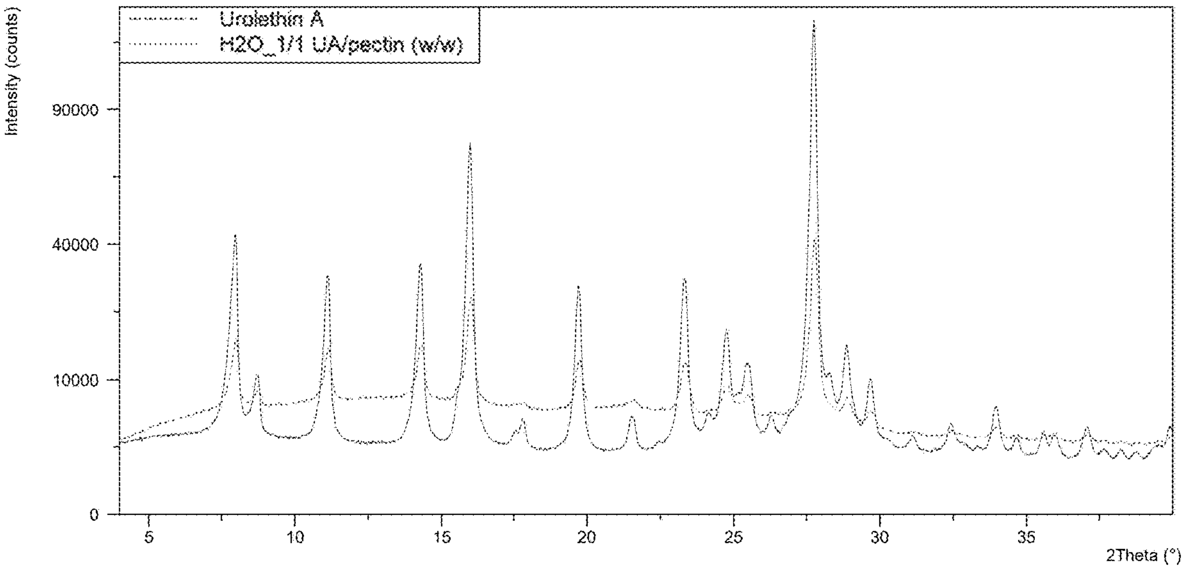
FIG. 9: An XRPD spectrum of urolithin A formulations, prepared by spray drying using water as solvent and using excipient pectin, complexed in a ratio of 1 to 1, urolithin A to excipient.

This was confirmed by calculating the area under the curve (AUC) of the dissolution profiles, in order to quantify the total presence of soluble UA over time. All UA/Pectin powders showed a significant increase in AUC (FIG. 6). Surprisingly the increase in AUC was not proportional, with ratio 7:1 showing the highest AUC (FIG. 8).

In summary, the data indicates that UA solubility can be increased significantly when UA is spray dried at certain ratio with pectin as excipient. Solubility enhancement is more pronounced with water is used as solvent. In addition, we show that even simple physical mixing of UA and pectin at certain ratio allow UA solubility improvement, with UA/Pectin 7/1 being the ratio leading to the best results.

Figure 10:
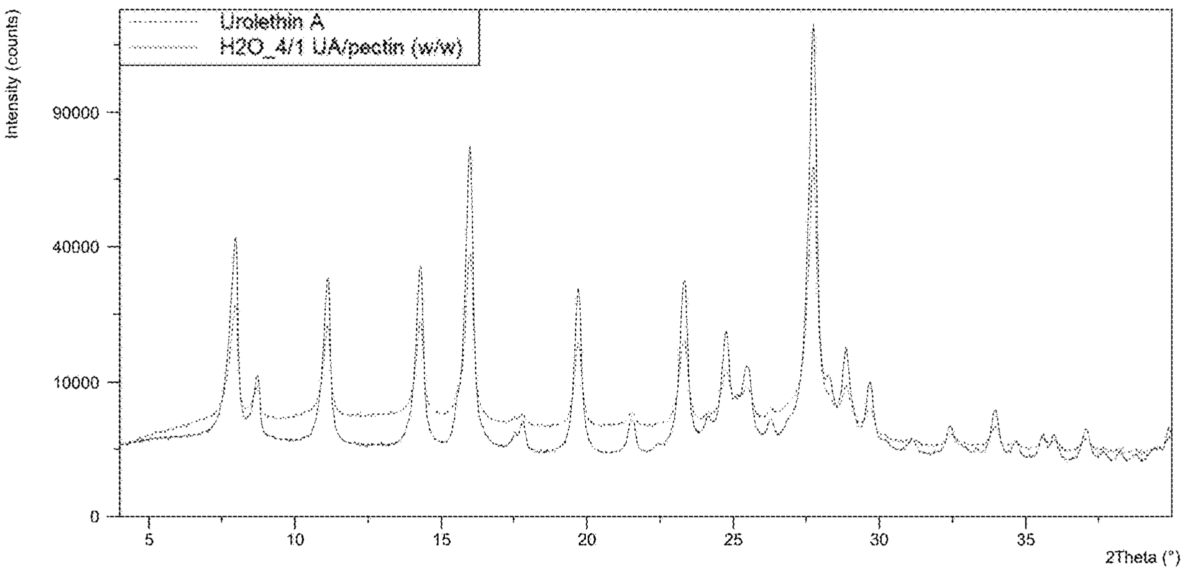
FIG. 10: An XRPD spectrum of urolithin A formulations, prepared by spray drying using water as solvent and using excipient pectin, complexed in a ratio of 4 to 1, urolithin A to excipient.

Example 5: Methodology for Preparation of Spray-Dried Urolithin A Formulations 1. Equipment Set-Up Spray drying trials were performed on the PROCEPT 4M8-TRIX spray dryer open loop system (i.e. atmospheric conditions/compressed gas) (FIG. 10). The spray dryer was equipped with a large cyclone. The extended column was installed to increase the residence time of the droplets/particles in the heated chamber. For all trials a bi-fluid nozzle with a 1.0 mm orifice was used.

2. Preparation Solutions and Suspensions

All suspensions were prepared with a solid load of 4.00% (w/w) in a total quantity of 50 g. For each formulation, this quantity was completely spray dried, resulting in 2 g of total dosed solids. Depending on the used UA/pectin w/w ratio, different amounts of UA and pectin were added.

For solvents ethanol and water, UA was firstly suspended in the solvent, followed by addition of the excipient Pectin. If UA and/or the excipient did not dissolve, formulation was spray dried as a suspension. Suspension was magnetically stirred for minimal 1 hour prior to processing. Also, during the spray drying process, suspensions were continuously stirred.

The non spray dried formulations were prepared by addition of UA powder and Pectin powder at different ratio tested. Powders were mixed using mortar and pestle until content was visually uniform.

Example 6-XRPD Evaluation of Urolithin A Samples

Urolithin A crystallinity was measured using X-ray powder diffraction (XRPD). XRPD diffractograms of crystalline urolithin A show a number of peak indicative of the crystal structure. In amorphous material these peaks are lost or at the very least much reduced. For example, an XRPD diffractogram of crystalline urolithin A is shown in FIG. 1.

The XRPD analysis was conducted under the following conditions.

Equipment: *Aeris* diffractometer (PANalytical, malvern) equipped with Cu tube (Ka)=1.5418 Å) Generator: 40 kV and 15 mA Sample: zero background sample holders Method
- continuous scan mode from 4° to 40°
- step size=0.0217°
- counting time 500 s

Example 7-UPLC Method-Assay Method

The release profile of the sample was analysed using an AT Xtend semi-automatic dissolution bath (Sotax) coupled CP piston pump (Sotax). An USP II (paddle) method was used with FaSSIF (pH 6.5) as dissolution medium at a temperature of 37° C. The paddle was rotated at 50 rpm.

Approximately 10 mg of UA was brought into 1000 ml of medium representing a maximum concentration of 0.01 mg/ml. Samples (i.e. 1.5 mL) of the medium were taken at set time points by a piston pump directly into UPLC vials. No dilution step was required, these samples were injected as such. Each sample was analysed in triplicate. Concentration was calculated by a calibration curve of UA, which was made in organic medium (dissolving in DMSO and dilution with ACN).

Chromatographic conditions:

System: UPLC

Detector: PDA (250-350 nm)-optimal wavelength: 230 nm

Column: SunFire C18 column, 100A, 3.5 μm, 4.6×150 mm

Flow rate: 1.2 mL/min

Column temperature: 40° C.

Injection volume: 7 μl

Run time: 25 min

Needle wash (Sample manager wash): MeOH/H2O (9/1, v/v)

Seal wash: MeOH/H2O (3/7, v/v)

Purge solvent (Sample manager purge): MeOH/H2O (3/7, v/v)

Mobile phase: A: 0.05% TFA (w/v) in H2O

B: 0.05% TFA (w/v) in ACN

| Time | 0 | 2.0 | 10 | 12 | 12.1 | 15 |
|---|---|---|---|---|---|---|
| % A | 95 | 95 | 10 | 10 | 95 | 95 |
| % B | 5 | 5 | 90 | 90 | 5 | 5 |

Equivalents

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Incorporation by Reference

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right physically to incorporate into this application any and all materials and information from any such articles, patents, patent applications, or other physical and electronic documents.

Embodiments of the Invention

1. A chewable formulation comprising:

a) a gelling component, b) a compound of formula (I) or a salt thereof:

(I)

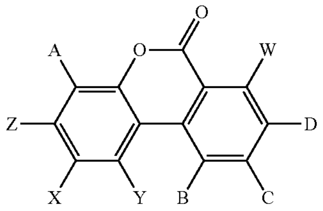

wherein:

A, B, C and D are each independently selected from H and OH;

W, X and Y are each independently selected from H and OH; and

Z is selected from H and OH; and wherein the formulation does not include a sweetener system.

2. A chewable formulation, as recited in Embodiment 1, further comprising:

c) a sweetener system, for example, wherein the sweetener system comprises one or more artificial sweeteners and/or comprises allulose.

3. A chewable formulation, as recited in Embodiment 2, wherein the sweetener system consists of one or more artificial sweeteners.

4. A chewable formulation, as recited in any one of the preceding Embodiments, wherein the gelling component comprises one or more of the following: pectin, gelatine, agar, corn starch and modified starch.

5. A chewable formulation, as recited in Embodiment 4, wherein the gelling component comprises pectin, for example, high methoxy pectin.

6. A chewable formulation, as recited in Embodiment 5, wherein the high methoxy pectin has an esterification range of about 60% to about 68%.

7. A chewable formulation, as recited in any one of the preceding Embodiments, wherein the formulation comprises about 0.5% to about 5% (w/w) gelling component, for example about 0.5% to about 3% (w/w) pectin, such as about 1.5% to about 3% (w/w) pectin.

8. A chewable formulation, as recited in any one of the preceding Embodiments, further comprising:

d) a fibre component, for example, a soluble fibre component.

9. A chewable formulation, as recited in Embodiment 8, wherein the fibre component is selected from: soluble tapioca, *psyllium* husk powder, apple fibre or mixtures thereof.

10. A chewable formulation as recited in any one of the preceding Embodiments, wherein the formulation has a brix between about 75 degrees to about 85 degrees.

11. A chewable formulation as recited in any one of the preceding Embodiments, wherein the formulation has a terminal boiling point between about 108° C. to about 111° C.

12. A chewable formulation as recited in any one of the preceding Embodiments, wherein the formulation comprises less than about 30% (w/w) sugar.

13. A chewable formulation as recited in any one of the preceding Embodiments, wherein the compound of Formula (I) is selected from urolithin A, urolithin B, urolithin C or urolithin D, for example, urolithin A 14. A chewable formulation as recited in any one of the preceding Embodiments, wherein the compound of formula (I) is present in the ranges 100 mg to 2500 mg.

15. A chewable formulation as recited in any one of the preceding Embodiments for use as a medicament, dietary supplement, functional food or medical food.

16. A chewable formulation as recited in any one of the preceding Embodiments for use as a medicament for use in the treatment and/or prophylaxis of a muscle-related pathological condition, for example, wherein the muscle-related pathological condition is selected from musculoskeletal diseases or disorders; muscle wasting; myopathies; neuromuscular diseases, such as Duchenne muscular dystrophy and other dystrophies; sarcopenia, for example, acute sarcopenia; muscle atrophy and/or cachexia.

17. A method of enhancing muscle performance, of improving endurance capacity, or of improving, maintaining or reducing the loss of muscle function comprising administering to a subject an effective amount of a chewable formulation as recited in any one of Embodiments 1 to 15, for example, wherein the subject suffers age-related decline in muscle function, age-related sarcopenia, age-related muscle wasting, physical fatigue, muscle fatigue, and/or is frail or pre-frail.

18. The use of a chewable formulation as recited in any one of Embodiments 1 to 15 in a method of improving physical performance, for example, wherein the improvement in physical performance is in a healthy individual or in the elderly.

19. The use of a chewable formulation as recited in any one of Embodiments 1 to 15 in a method of increasing muscle strength, increasing or maintaining muscle mass or improving muscle recovery.

20. The use of a chewable formulation as recited in any one of Embodiments 1 to 15 in a method of improving physical endurance.

21. The use of a chewable formulation as recited in any one of Embodiments 1 to 15 in a method of inhibiting or retarding physical fatigue, enhancing working capacity and endurance, reducing muscle fatigue, enhancing cardiac and cardiovascular function.

22. The use of a chewable formulation as recited in any one of Embodiments 1 to 15 in a method of enhancing sports performance.

23. The use of a chewable formulation as recited in any one of Embodiments 1 to 15 for non-disease health conditions characterised by inadequate mitochondrial activity.

24. A formulation as recited in any one of Embodiments 1 to 15 for use in treating disease conditions characterised by inadequate mitochondrial activity.

What is claimed is:

1. A composition comprising urolithin A or a salt thereof; and pectin; wherein the ratio of urolithin A to pectin is about 1:2 (w/w) to about 10:1 (w/w).

2. The composition of claim 1, wherein the pectin is selected from low methoxyl pectin, high methoxyl pectin, and amidated low methoxyl pectin, or a mixture of any of them.

3. The composition of claim 2, wherein the pectin is an amidated low methoxyl pectin.

4. The composition of claim 1, wherein the amount of urolithin A or salt thereof is about 1% to about 20% (w/w).

5. The composition of claim 4, wherein the amount of urolithin A or salt thereof is about 5% to about 15% (w/w).

6. The composition of claim 4, wherein the amount of urolithin A or salt thereof is about 5% to about 10% (w/w).

7. The composition of claim 1, wherein the amount of pectin is about 0.5% to about 4% (w/w).

8. The composition of claim 7, wherein the amount of pectin is about 0.5% to about 3% (w/w).

9. The composition of claim 1, further comprising one or more low-calorie sweeteners.

10. The composition of claim 9, wherein the one or more low-calorie sweeteners is selected from *stevia* and fructooligosaccharide.

11. The composition of claim 1, further comprising soluble fibre.

12. The composition of claim 11, wherein the soluble fibre is soluble tapioca fibre or inulin-derived fibre.

13. The composition of claim 1, further comprising a citrate salt.

14. The composition of claim 13, wherein the citrate salt is sodium citrate.

15. The composition of claim 1, further comprising one or more low-calorie sweeteners; soluble fibre; and a citrate salt.

16. The composition of claim 15, wherein the amount of urolithin A or salt thereof is about 1% to about 20% (w/w).

17. The composition of claim 16, wherein the amount of pectin is about 0.5% to about 4% (w/w).

18. The composition of claim 17, wherein the amount of one or more low-calorie sweeteners is about 25% to about 45% (w/w); the amount of soluble fibre is about 25% to about 45% (w/w); and the amount of citrate salt is about 0.1% to about 2% (w/w).

19. The composition of claim 18, wherein the pectin is selected from low methoxyl pectin, high methoxyl pectin, and amidated low methoxyl pectin, or a mixture of any of them.

20. The composition of claim 19, wherein the pectin is amidated low methoxyl pectin extracted from citrus peel.

21. The composition of claim 18, wherein the soluble fibre is soluble tapioca fibre.

22. The composition of claim 18, wherein the one or more low-calorie sweeteners is selected from *stevia* and fructooligosaccharide.

23. The composition of claim 18, wherein the citrate salt is sodium citrate.

24. The composition of claim 1, wherein the composition is in the form of a gummy.

25. The composition of claim 1, wherein the amount of urolithin A or salt thereof is about 100 mg to about 2500 mg.

26. The composition of claim 1, wherein the amount of urolithin A or salt thereof is about 1000 mg.

27. The composition of claim 1, wherein the amount of urolithin A or salt thereof is about 500 mg.

28. The composition of claim 1, wherein the amount of urolithin A or salt thereof is about 250 mg.

29. The composition of claim 1, wherein the amount of urolithin A or salt thereof is about 5% to about 20% (w/w); and the amount of pectin is about 0.5% to about 5% (w/w).

30. The composition of claim 10, comprising *stevia* in amount of about 0.001% to about 3% (w/w).

* * * * *